(12) United States Patent
Umemoto et al.

(10) Patent No.: US 8,203,003 B2
(45) Date of Patent: Jun. 19, 2012

(54) 4-FLUOROPYRROLIDINE-2-CARBONYL FLUORIDE COMPOUNDS AND THEIR PREPARATIVE METHODS

(75) Inventors: Teruo Umemoto, Denver, CO (US); Rajendra P. Singh, Denver, CO (US)

(73) Assignee: UBE Industries, Ltd., Tokyo (JP)

( * ) Notice: Subject to any disclaimer, the term of this patent is extended or adjusted under 35 U.S.C. 154(b) by 0 days.

(21) Appl. No.: 13/143,026

(22) PCT Filed: Jan. 8, 2010

(86) PCT No.: PCT/US2010/020515
§ 371 (c)(1),
(2), (4) Date: Jun. 30, 2011

(87) PCT Pub. No.: WO2010/081014
PCT Pub. Date: Jul. 15, 2010

(65) Prior Publication Data
US 2011/0275833 A1    Nov. 10, 2011

Related U.S. Application Data

(60) Provisional application No. 61/143,473, filed on Jan. 9, 2009, provisional application No. 61/148,232, filed on Jan. 29, 2009.

(51) Int. Cl.
*C07D 207/10* (2006.01)
*C07D 207/12* (2006.01)
*A61K 31/40* (2006.01)
(52) U.S. Cl. ......... 548/406; 548/530; 548/536; 514/423
(58) Field of Classification Search .................. None
See application file for complete search history.

(56) References Cited

U.S. PATENT DOCUMENTS

| | | | |
|---|---|---|---|
| 3,054,661 A | 9/1962 | Muetterties | |
| 3,919,204 A | 11/1975 | Boswell, Jr. et al. | |
| 4,147,733 A | 4/1979 | Fiske et al. | |
| 4,316,906 A | 2/1982 | Ondetti et al. | |
| 5,055,223 A | 10/1991 | Reiffenrath et al. | |
| 5,093,432 A | 3/1992 | Bierschenk et al. | |
| 5,395,916 A | 3/1995 | Mochizuki et al. | |
| 5,455,373 A | 10/1995 | Kawa | |
| 5,691,081 A | 11/1997 | Krause et al. | |
| 5,741,935 A | 4/1998 | Bowden et al. | |
| 5,789,580 A | 8/1998 | Chambers et al. | |
| 5,824,827 A | 10/1998 | Bildinov et al. | |
| 6,222,064 B1 | 4/2001 | Lal et al. | |
| 6,737,193 B2 | 5/2004 | Umemoto | |
| 6,958,415 B2 | 10/2005 | Lal et al. | |
| 7,015,176 B2 | 3/2006 | Bailey, III et al. | |
| 7,045,360 B2 | 5/2006 | Shair et al. | |
| 7,087,681 B2 | 8/2006 | Umemoto | |
| 7,265,247 B1 | 9/2007 | Umemoto et al. | |
| 7,279,584 B2 | 10/2007 | Tomisawa et al. | |
| 7,351,863 B2 | 4/2008 | Hara et al. | |
| 7,381,846 B2 | 6/2008 | Umemoto et al. | |
| 7,501,543 B2 | 3/2009 | Umemoto et al. | |
| 7,592,491 B2 | 9/2009 | Umemoto | |
| 7,820,864 B2 | 10/2010 | Umemoto et al. | |
| 7,851,646 B2 | 12/2010 | Umemoto | |
| 7,919,635 B2 | 4/2011 | Umemoto | |
| 8,030,516 B2 | 10/2011 | Umemoto et al. | |
| 2001/0021792 A1 | 9/2001 | Nakada et al. | |
| 2001/0049457 A1 | 12/2001 | Stephens | |
| 2003/0060669 A1 | 3/2003 | Shibata et al. | |
| 2004/0022720 A1 | 2/2004 | Low et al. | |
| 2004/0106827 A1 | 6/2004 | Dolbier et al. | |
| 2004/0209854 A1 | 10/2004 | Barkalow et al. | |
| 2004/0249209 A1 | 12/2004 | Bailey, III et al. | |
| 2005/0012072 A1 | 1/2005 | Bailey, III et al. | |
| 2005/0148652 A1 | 7/2005 | Kleemann et al. | |
| 2006/0014972 A1 | 1/2006 | Hara et al. | |
| 2009/0105502 A1 | 4/2009 | Umemoto et al. | |
| 2009/0203924 A1 | 8/2009 | Umemoto et al. | |
| 2009/0287024 A1 | 11/2009 | Umemoto et al. | |
| 2010/0029992 A1 | 2/2010 | Umemoto et al. | |
| 2010/0076215 A9 | 3/2010 | Umemoto et al. | |
| 2010/0152463 A1 | 6/2010 | Umemoto et al. | |
| 2010/0174096 A1 | 7/2010 | Umemoto et al. | |
| 2010/0234605 A1 | 9/2010 | Umemoto et al. | |
| 2011/0004022 A1 | 1/2011 | Umemoto | |
| 2011/0009672 A1 | 1/2011 | Umemoto | |
| 2011/0160488 A1 | 6/2011 | Umemoto | |
| 2011/0166392 A1 | 7/2011 | Umemoto | |
| 2011/0190511 A1 | 8/2011 | Umemoto et al. | |
| 2011/0301382 A1 | 12/2011 | Umemoto et al. | |

(Continued)

FOREIGN PATENT DOCUMENTS

DE    19748109 A1    5/1999

(Continued)

OTHER PUBLICATIONS

Umemoto et al (2010) "Discovery of 4-tert-Butyl-2,6-dimethylphenylsulfur Trifluoride as a Deoxofluorinating Agent with High Thermal Stability as Well as Unusual Resistance to Aqueous Hydrolysis, and Its Diverse Fluorination Capabilities Including Deoxofluoro-Arylsulfinylation with High Stereoselectivity" JACS 132:18199-18205.

Andrieux et al. (1990) "Outer-sphere and inner-sphere processes in organic chemistry. Reaction of trifluoromethyl bromide with electrochemically generated aromatic anion radicals and sulfur dioxide anion radicals" J. Am. Chem. Soc. 112(2): 786-791.

Bégué and Bonnet-Delpon (2006) "Recent Advances (1995-2005) in Fluorinated Pharmaceuticals Based on Natural Products" Journal of Fluorine Chemistry 127:992-1012+A3.

Bowden et al. (2000) "A New Method for the Synthesis of Aromatic Sulfurpentafluorides and Studies of the Stability of the Sulfurpentafluoride Group in Common Synthetic Transformation" Tetrahedron 56:3399-3408.

(Continued)

*Primary Examiner* — Yong Chu
*Assistant Examiner* — Michael Barker
(74) *Attorney, Agent, or Firm* — Swanson & Bratschun, L.L.C.

(57) ABSTRACT

Novel 4-fluoropyrrolidine-2-carbonyl fluoride compounds as useful fluorinated intermediates are disclosed. Their preparative methods are also disclosed. Useful applications of the 4-fluoropyrrolidine-2-carbonyl fluorides are shown.

15 Claims, No Drawings

U.S. PATENT DOCUMENTS

2011/0306798 A1    12/2011    Umemoto

FOREIGN PATENT DOCUMENTS

| | | |
|---|---|---|
| EP | 0361907 A2 | 4/1990 |
| EP | 1484318 A1 | 12/2004 |
| GB | 2276379 | 9/1994 |
| JP | H02-154266 A | 6/1990 |
| JP | 2003-077861 | 4/1991 |
| JP | H07-292050 A | 11/1995 |
| JP | H09-500893 A | 1/1997 |
| JP | 2000-38370 A | 8/2000 |
| JP | 2004-359687 A | 12/2004 |
| JP | 4531852 | 6/2010 |
| TW | 270111 | 2/1996 |
| TW | I 325857 | 6/2010 |
| TW | I 327135 | 7/2010 |
| WO | WO 94/21606 | 9/1994 |
| WO | WO 01/27076 | 4/2001 |
| WO | WO 03/002553 | 1/2003 |
| WO | WO 2004/011422 | 2/2004 |
| WO | WO 2004/050676 | 6/2004 |
| WO | WO 2008/013550 | 1/2008 |
| WO | WO 2008/014345 | 1/2008 |
| WO | WO 2008/118787 | 10/2008 |
| WO | WO 2009/076345 | 6/2009 |
| WO | WO 2009/114409 | 9/2009 |
| WO | WO 2010/014665 | 2/2010 |
| WO | WO 2010/022001 | 2/2010 |
| WO | WO 2010/033930 | 3/2010 |
| WO | WO 2010/081014 | 7/2010 |

OTHER PUBLICATIONS

Bunnelle et al. (1990) "Difluorination of Esters. Preparation of $\alpha$, $\alpha$-Difluoro Ethers" J. Org. Chem. 55(2):768-770.

Calamari and Trask (1979) "Laboratory Explosions" Chemical & Engineering News, 57(19):4.

Cava and Levinson (1985) "Thionation Reactions of Lawesson's Reagents" Tetrahedron 41(22):5061-5087.

Chambers et al. (1996) "Elemental Fluorine. Part 5.1,2 Reactions of 1,3-Dithiolanes and Thioglycosides With Fluorine-Iodine Mixtures" J. Chem. Soc. Perkin Trans. 1 1941-1944.

Cochran (Mar. 19, 1979) "Laboratory Explosions" Chemical & Engineering News 57(19):4.

Davis et al (1999) "Efficient Asymmetric Synthesis of $\beta$-Fluoro $\alpha$-Amino Acids" J. Org. Chem. 64:6931-6934.

Des Marteau (1995) "Novel perfluorinated ionomers and ionenes" J. Fluorine Chem. 72(2): 203-208.

Feiring (1979) "Chemistry in Hydrogen Fluoride. 7. A Novel Synthesis of Aryl Trifluoromethyl Ethers" J. Org. Chem. 44(16):2907-2910.

Folest et al. (1988) "Electrochemical Synthesis of Trifluoromethane Sulfinic Acid Salt From CF3Br and SO2" Synthetic Communications 18(13): 1491-1494.

Furuya et al. (2005) "Synthesis of gem-difluorides From Aldehydes Using DFMBA" Journal of Fluorine Chemistry 126:721-725.

Hasek et al. (1960) "The Chemistry of Sulfur Tetrafluoride. II. The Fluorination of Organic Carbonyl Compounds" Journal of American Chem. Soc. 82(3):543-551.

Hayashi et al. (2002) "2,2-Difluoro-1,3-dimethylimidazolidine (DFI). A New Fluorinating Agent" Chem. Commun. 1618-1619.

Henne and Nager (1951) "Trifluoropropyne" J. Am. Chem. Soc. 73(3):1042-1043.

Hollitzer and Sartori (1987) "The electrochemical perfluorination (ECPF) of propanesulfonyl fluorides. I: Preparation and ECPF of 1-propanesulfonyl fluoride and 1,3-propanedisulfonyl difluoride" J. Fluorine Chem. 35(2): 329-341.

Hoover and Coffman (1964) "Synthesis and Chemistry of Ethynylsulfur Pentafluoride" Journal of Organic Chem. 29:3567-3570.

Howe-Grant (1995) "Sulfur Hexafluoride" Fluorine Chemistry: A Comprehensive Treatment, John Wiley & Sons, Inc. , New York (ISBN: 0-471-12031-6) pp. 188-195.

Hu and DesMarteau (1993) "Synthesis of Perhaloalkanesulfonyl Halides and Their Sulfonimide Derivatives" Inorg. Chem. 32:5007-5010.

Huang and Guo (1981) "The Reaction of Arylsulfur Trifluoride With Sterols" Shanghai Institute of Organic Chemistry, ACTA Chimica Sinica 39(1):68.

Huang and Lu (1992) "The Reaction of Perfluoroalkanesylfonyl Halides" Chinese Journal of Chemistry Chapter VII 10(3):268-273.

Huang and Lu (1992) "The Reaction of Perfluoroalkanesylfonyl Halides" Chinese Journal of Chemistry Chapter VIII 10(3):274-277.

Kirsch and Bremer (2000) "Nematic Liquid Crystals for Active Matrix Displays: Molecular Design and Synthesis" Angew. Chem. Int. Ed. 39:4216-4235.

Kirsch and Hahn (2005) "Liquid Crystals Based on Hypervalent Sulfur Fluorides: Exploring the Steric Effects of ortho-Fluorine Substituents" Eur. J. of Org. Chem. 3095-3100.

Kobayashi et al.(2004) "Deoxyfluorination of alcohols using N,N-diethyl-$\alpha$, $\alpha$-difluoro-(m-methylbenzyl)amine" Tetrahedron 60:6923-6930.

Kuroboshi et al. (1992) "Oxidative Desulfurization-Fluorination of Xanthates. A Convenient Synthesis of Trifluoromethyl Ethers and Difluoro(methylthio)methyl Ethers" Tetrahedron 33(29): 4173-4176.

Kuroboshi and Hiyama (1991) "A Facile Synthesis of Difluoromethylene Compounds by Oxidative Fluorodesulfurization of Dithioacetals Using Tetrabutylammonium Dihydrogentrifluoride and N-Halo Compounds" Synlett 909-910.

Kuroboshi and Hiyama (1992) "A Facile Synthesis of Trifluoromethylamines by Oxidative Desulfurization-Fluorination of Dithiocarbamates" Tetrahedron 33(29):4177-4178.

Kuroboshi and Hiyama (1992) "Oxidative Desulfurization-Fluorination of Methyl Arenedithiocarboxylates. A Convenient Synthesis of Trifluoromethylated Aromatic Compounds" Chemistry Letters 827-830.

Kuroboshi and Hiyama (1994) "A Convenient Synthesis of Perfluoroalkylated Amines by Oxidative Desulfurization-Fluorination" Tetrahedron 35(23):3983-3984.

Kuroboshi and Hiyama (1994) "A Facile Synthesis of $\alpha$, $\alpha$-Difluoroalkyl Ethers and Carbonyl Fluoride Acetals by Oxidative Desulfurization-Fluorination" Synlett 251-252.

Lal et al. (1999) "Bis(2-methoxyethyl)aminosulfur trifluoride: a new broad-spectrum deoxofluorinating agent with enhanced thermal stability" Chem. Commun.215-216.

Lal et al. (2000) "Fluorination of Thiocarbonyl Compounds with Bis(2-methoxyethyl)aminosulfur Trifluoride (Deoxo-Fluor Reagent): A Facile Synthesis of gem-Difluorides" J. Org. Chem. 65:4830-4832.

Lee et al. (1989) "One Pot Phase Transfer Synthesis of O-Alkyl, S-Methyl Dithiocarbonates (Xanthates)" Synthetic Communications 19(3&4):547-552.

Ma and Cahard (2007) "Strategies for Nucleophilic, Electrophilic, and Radical Trifluoromethylations" Journal of Fluorine Chemistry 128:975-996.

Mayer and Scheithauer (1985) Carbonsäuren und Carbonsäure-Derivate E5:891-916.

Methods of Organic Chemistry (Houben-Weyl), Work Bench Edition vol. E 10A, Organo-Fluorine Compounds, Gorge Thieme Verlag Stuttgart, New York, 2000 pp. 194-201.

Middleton (1975) "New Fluorinating Reagents. Dialkylaminosulfur Fluorides" Journal of Organic Chem. 40(5):574-578.

Moss et al. (1995) "Glossary of Class Names of Organic Compounds and Reactive Intermediates Based on Structure" Pure & Appl. Chem, 67(8/9):1307-1375.

Motherwell and Wilkinson (1991) "Observations on the Reaction of Dithioketals with Para-Iodotoluene Difluoride: A Novel Route to Gem-Difluoro Compounds" Synlett 191-192.

Notice of Allowance mailed Jul. 26, 2011 with respect to U.S. Appl. No. 12/253,030.

Notice of Allowance mailed Jun. 21, 2011 with respect to U.S. Appl. No. 12/253,030.

Notice of Allowance mailed Dec. 7, 2010 with respect to U.S. Appl. No. 12/367,171.

Notice of Allowance mailed Oct. 28, 2010 with respect to U.S. Appl. No. 12/367,171.
Notice of Allowance mailed Jun. 23, 2010 with respect to U.S. Appl. No. 12/473,109.
Notice of Allowance mailed Aug. 6, 2010 with respect to U.S. Appl. No. 12/473,129.
Notice of Allowance mailed Oct. 31, 2008 with respect to U.S. Appl. No. 12/106,460.
Notice of Allowance mailed Apr. 29, 2009 with respect to U.S. Appl. No. 12/053,775.
Office Action mailed Aug. 4, 2011 with respect to U.S. Appl. No. 12/647,973.
Office Action mailed Jun. 1, 2011 with respect to U.S. Appl. No. 12/633,414.
Office Action mailed Jan. 21, 2011 with respect to U.S. Appl. No. 12/305,868.
Office Action mailed Sep. 13, 2010 with respect to U.S. Appl. No. 12/633,414.
Office Action mailed Mar. 2, 2010 with respect to U.S. Appl. No. 12/473,129.
Office Action mailed Jan. 7, 2010 with respect to U.S. Appl. No. 12/473,109.
Office Action mailed Oct. 22, 2009 with respect to U.S. Appl. No. 12/367,171.
Office Action mailed Nov. 20, 2007 with respect to U.S. Patent No. 7,381,846.
Office Action mailed Dec. 3, 2008 with respect to U.S. Patent No. 7,592,491.
Oae, Shigeru (1977) "Sulfoxides and Sulfilimines" Organic Chemistry of Sulfur, Plenum Press, NY and London, Chapters 8 and 10, pp. 384-589.
Oae, Shigeru (1977) "Sulfoxides and Sulfilimines" Organic Chemistry of Sulfur, Plenum Press, NY and London, Chapter 10, Section 10.3.7, pp. 572-577.
Olah et al. (1974) "Synthetic Methods and Reactions. I. Selenium Tetrafluoride and Its Pyridine Complex. Convenient Fluorinating Agents for Fluorination of Ketones, Aldehydes, Amides, Alcohols, Carboxylic Acids, and Anhydrides" Journal of American Chem. Soc. 96(3):925-927.
Ou et al. (1997) "Oxidative Addition and Isomerization Reactions. The Synthesis of cis- and trans-ArSF4C1 and cis- and trans-PHTeF4C1" Can. Journal of Chem. 75:1878-1884.
Ou and Janzen (2000) "Oxidative Fluorination of S, Se and Te Compounds" Journal of Fluorine Chem. 101:279-283.
Pashinnik et al. (2003) "A New Method for the Synthesis of Organosulfur Trifluorides" Synthetic Communications 33(14):2505-2509.
Patai and Rappoport (1994) "Synthesis of Sulphoxides" The Synthesis of Sulphones, Sulphoxides and Cyclic Sulphides, John Wiley & Sons, An Interscience Publication, Chapter 3, pp. 109-158.
Petrov et al. (2001) "1,1,2,2-Tetrafluoroethyl-N,N-dimethylamine: A New Selective Fluorinating Agent" Journal of Fluorine Chemistry 109:25-31.
Petrov et al. (2004) "Quadricyclane—thermal cycloaddition to polyfluorinated carbonyl compounds: A simple synthesis of polyfluorinated 3-oxatricyclo[4.2.1.02,5]non-7-enes" Journal of Fluorine Chem. 125(10): 1543-1552.
Prakash et al. (1993) "Simplified Preparation of α,α-Difluorodiphenlmethanes From Benzophenone 1,3-Dithiolanes With Sulfuryl Choride and Pyridinium Polyhydrogen Fluoride" Synlett 691-693.
Qiu and Burton (1993) "A useful synthesis of ω-iodoperfluoroalkanesulfonyl fluorides and perfluoroalkane-α,ω-bis-sulfonyl fluorides" J. Fluorine Chem. 60(1): 93-100.
Reddy et al. (2005) "gem-Difluorination of 2,2-Diaryl-1,3-dithiolanes by Selectfluor® and Pyridinium Polyhydrogen Fluoride" Chem. Commun. 654-656.

Rozen and Mishani (1993) "Conversion of Esters to α, α-Difluoro Ethers Using Bromine Trifluoride" J. Chem. Soc. Commun. 1761-1762.
Sasson et al. (2003) "Novel Method for Incorporating the CHF2 Group into Organic Molecules Using BrF3" Organic Letters 5(5):769-771.
Scheeren et al. (1973) "A General Procedure for the Conversion of a Carbonyl Group into a Thione Group with Tetraphosphorus Decasulfide" Communications 149-151.
Seergeva and Dolbier (2004) "A New Synthesis of Pentafluorosulfanylbenzene" Organic Letters 6(14):2417-2419.
Sharts and Sheppard (1974) "Modern Methods to Prepare Monofluoroaliphatic Compounds" Organic Chemistry 21:158-173.
Sheppard (1962) "Arylsulfur Pentafluorides" J. Am. Chem. Soc. 84:3064-3072.
Sheppard (1962) "Alkyl- and Arylsulfur Trifluorides" J. Chem. Soc. 84:3058-3063.
Sheppard (1973) "Phenylsulfur Tri Fluoride" Organic Syntheses, Coll. 5:959; (1964) 44:82.
Sheppard and Foster (1972) "Pentafluorophenylsulfur(IV) Derivatives" Journal of Fluorine Chemistry 2:53-61.
Sheppard and Taft (1972) "The Electronic Properties of Di-, Tri-, Tetra-, and Hexacoordinate Sulfur Substituents" Journal Am. Chem. Soc. 94(6)1919-1923.
Shimizu et al. (1995) "Gem-Difluorination of 1,3-Dithiolanes with the Hexafluoropropene-Diethylamine reagent and N-Iodosuccinimide or 1,3-Dibromo-5,5-Dimethylhydantoin" Journal of Fluorine Chemistry 71:9-12.
Simons and Lewis (1938) "The Preparation of Benzotrifluoride" J. Am. Chem. Soc. 60(2):492.
Sipyagin et al. (2001) "Preparation of the First Ortho-Substituted Pentafluorosulfanylbenzenes" Journal of Fluorine Chemistry 112:287-295.
Smith et al. (1960) "Chemistry of Sulfur Tetrafluoride. III. Organoiminosulfur Difluorides" Journal of American Chem. Soc. 82(3):551-555.
Sondej and Katzenellenbogen (1986) "Gem-Difluoro Compounds: A Convenient Preparation from Ketones and Aldehydes by Halogen Fluoride Treatment of 1,3-Dithiolanes" J. Org. Chem. 51:3508-3513.
Tarrant et al. (1954) "Fluoroölefins. V. The Synthesis of 1,1-Difluoro-3-Methylbutadiene" J. Am. Chem. Soc. 76(9): 2343-2345.
Thayer (2006) "Fabulous Fluorine" Chemical & Engineering News 84(23):15-24.
Thayer (2006) "Constructing Life Sciences Compounds" Chemical & Engineering News 84(23):27-32.
Tordeux et al. (1990) "Reactions of trifluoromethyl bromide and related halides: part 9. Comparison between additions to carbonyl compounds, enamines, and sulphur dioxide in the presence of zinc" J. Chem. Soc., Perkin Trans. 1 1951-1957.
Tozer and Herpin (1996) "Methods for the Synthesis of gem-Difluoromethylene Compounds" Tetrahedron 52(26): 8619-8683.
Tullock (1960) "The Chemistry of Sulfur Tetrafluoride. I. The Synthesis of Sulfur Tetrafluoride" Journal of American Chem. Soc. 82(3):539-542.
Uneyama (2006) "Nucleophilic Substitution on Fluoroaromatic Rings" Organofluorine Chemistry, Blackwell Publishing Ltd., Oxford, UK (ISBN-13: 978-14051-2561-1) pp. 101-107.
Whitham, Gordon H. (1995) "Organosulfur Chemistry" Oxford Chemistry Primers, 33, Oxford Science Publications, Chapter 3, pp. 34-63 (ISBN-13: 9780198558996).
Winter and Gard (2004) "Synthesis of SF5-benzene (SF5C6H5) by the SF5-halide Method" Journal of Fluorine Chem. 125:549-552.
Yoshiyama and Fuchigami (1992) "Anodic gem-Difluorination of Dithioacetals" Chemistry Letters 1995-1998.
Xiaobo et al. (1997) "Oxidative Addition and Isomerization Reactions—The Synthesis of cis-ArSF$_4$C1 and trans-ArSF$_4$C1 and cis-PhTeF$_4$C1 and trans-PhTeF$_4$C1" Canadian Journal of Chemistry, 75(12):1878-1884.

4-FLUOROPYRROLIDINE-2-CARBONYL FLUORIDE COMPOUNDS AND THEIR PREPARATIVE METHODS

RELATED APPLICATIONS

This application is a 35 U.S.C. §371 national phase application of PCT/US2010/020515 (WO 2010/081014), filed on Jan. 8, 2010, entitled "Novel 4-Fluoropyrrolidine-2-Carbonyl Fluoride Compounds and Their Preparative Methods", which application claims the benefit of U.S. Provisional Application Ser. No. 61/143,473, filed Jan. 9, 2009, and claims benefit of U.S. Provisional Application Ser. No. 61/148,232, filed Jan. 29, 2009, each of which are incorporated herein by reference in their entirety.

TECHNICAL FIELD

The invention relates to novel 4-fluoropyrrolidine-2-carbonyl fluoride compounds as useful intermediates in the production of 4-fluoropyrrolidine derivatives and to their preparative methods.

BACKGROUND OF THE INVENTION

4-Fluoropyrrolidine derivatives are particularly useful for medicinal applications and have been utilized in the development of therapeutics such as dipeptidyl peptidase (DPP) IV inhibitors, which serve for diabetes treatment etc. [see, for example, Bioorganic & Medicinal Chemistry, 2008, Vol. 16, pp. 4093-4106 (Taisho Pharm.); Bioorganic & Medicinal Chemistry Letters, 2007, Vol. 17, pp. 4167-4172 (LG Life Sci.); WO 03/002533 A2 (Smithkline Beecham); WO 2004/020407 A1 (Taisho Pharm.); WO 2004/009544 A1 (Yamanouchi Pharm.); Jpn Kokai Tokyo Koho JP 2004-244412 (Kotobuki Pharm.); WO 2005/075421 A1 (Kyorin Pharm.); WO 2006/043595 A1 (Astellas Pharm.); WO 2006/134613 A2 (Aurigene Discovery Tech.); WO 2008/001195 A2 (Glenmark Pharm.)], and peptide deformylase (PDF) inhibitor which is a novel class of antimicrobial agents [Organic Process Research & Development, 2008, Vol. 12, pp. 183-191 (Novartis Pharm.)]. However, there are a number of drawbacks in the conventional preparation of 4-fluoropyrrolidine derivatives, as is discussed more fully below.

For example, (2S,4S)-4-fluoropyrrolidine-2-carboxamide, its salts and N-protected derivatives (compounds F and G are shown in Scheme 1, below), are significant intermediate compounds for the preparation of DPP inhibitors [see, for example, Bioorganic & Medicinal Chemistry, Vol. 16 (2008), pp. 4093-4106 (Taisho Pharm.); WO 03/002533 A2 (Smithkline Beecham); Jpn Kokai Tokyo Koho JP 2004-244412 (Kotobuki Pharm.); WO 2006/134613 A2 (Aurigene Discovery Tech.); WO 2008/001195 A2 (Glenmark Pharm.); Jpn. Kokai Tokkyo Koho JP 2008-239543 (Kyorin Pharm.)]. The compounds F and G have been prepared as shown in Scheme 1, according to the literature [See WO 03/002553 A2 (Smithkline)]. A starting material, (2S,4R)-4-hydroxypyrrolidine-2-carboxylic acid (called as trans-4-hydroxy-L-proline) (compound A), is commercially available, isolated from gelatin (collagen). Compound A was (i) esterified, followed by (ii) N-substitution (N-protection), giving compound C (R=a protecting group) which was then, (iii) fluorinated with diethylaminosulfur trifluoride (DAST) to give compound D. Next, step (iv) was a careful hydrolysis of compound D with lithium hydroxide because of possible racemization, and in steps (v) and (vi) transformation of compound E to compound F, which consisted of two steps; a reaction step with di-tert-butyldicarbonate followed with ammonium hydrogen carbonate. N-Deprotection reaction of compound F gave compound G.

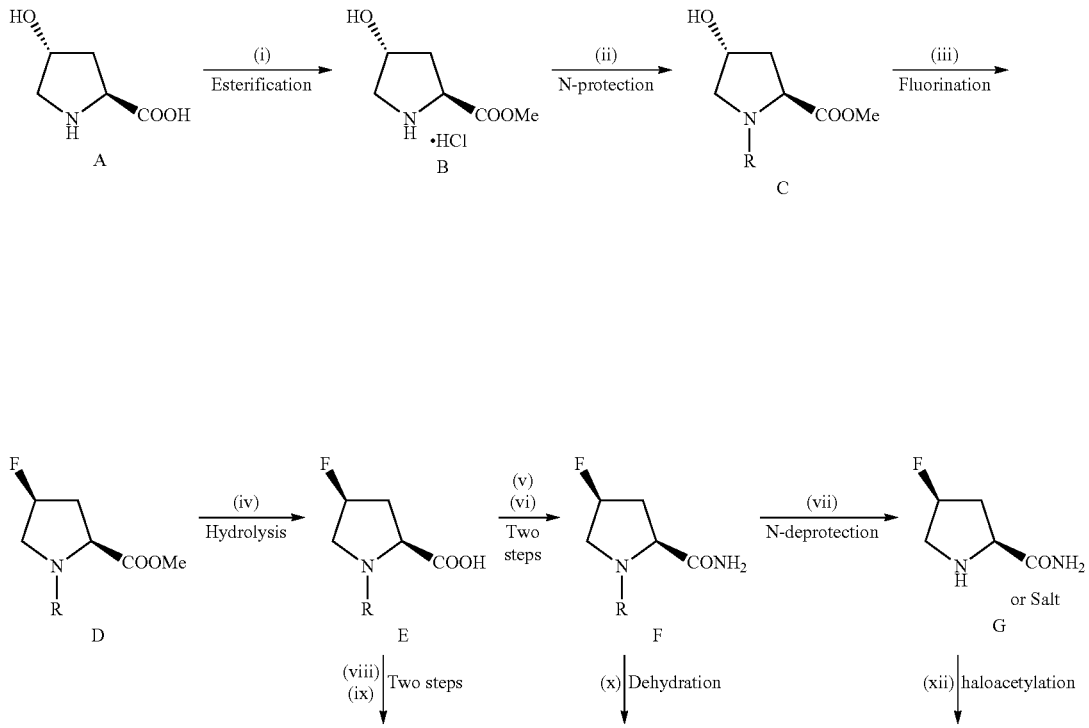

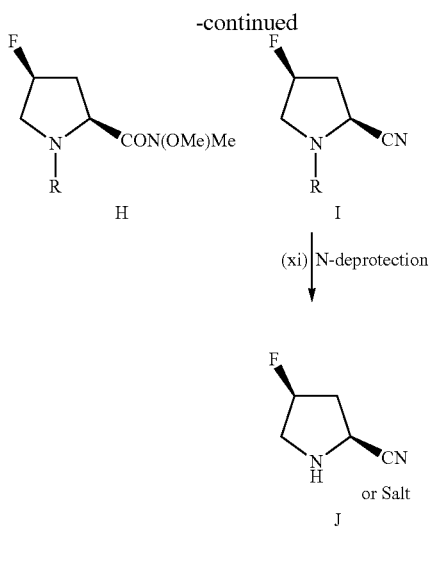
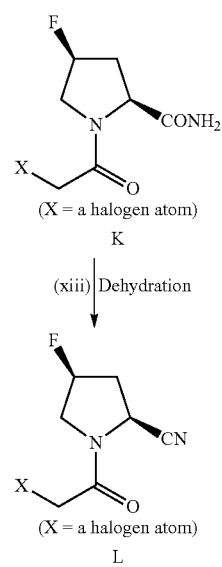

(2S,4S)—N-haloacetyl-4-fluoropyrrolidine-2-carboxamide, compound K shown in Scheme 1, is another important useful intermediate for the preparation of DPP IV inhibitors [see, for example, with regard to DPP IV inhibitors: WO 2007/113634 A1 (Matrix Laboratories, Ltd.); U.S. Pat. No. 7,186,731 B2 (Astellas Pharma Inc.); WO 2005/042533 A2 (Fujisawa Pharmaceutical CO, Ltd.); WO 2003/074500 A2 (Sanofi-Synthelabo)]. Compound K was prepared by step (xii), haloacetylation of compound G, which was therefore ultimately prepared from starting material compound A via a total of 8 steps, as shown in Scheme 1.

(2S,4S)—N-haloacetyl-4-fluoropyrrolidine-2-carbonitrile, compound L shown in Scheme 1, is another important intermediate for the preparation of the DPP IV inhibitors. Compound L was prepared by step (xiii), dehydration of compound K, as shown in Scheme 1.

N-protected (2S,4S)-4-fluoropyrrolidine-2-(N-methyl-N-methoxy)carboxamide, compound H shown in Scheme 1, is another useful intermediate for the preparation of DPP IV inhibitors [Bioorganic & Medicinal Chemistry Letters, 2007, Vol. 17, pp. 4167-4172; Organic Process Research & Development, 2008, Vol. 12, pp. 626-631]. Compound H was prepared by steps (viii) and (ix), a two-step transformation of compound E to compound H, as shown in Scheme 1 above.

(2S,4S)-4-Fluoropyrrolidine-2-carbonitrile, its salts and N-protected derivatives (compounds I and J shown in Scheme 1), are also useful intermediate compounds for the preparation of DDP IV inhibitors [see, for example, WO 03/002533 A2 (Smithkline Beecham); WO 2008/001195 A2 (Glenmark Pharm.); and Jpn. Kokai Tokkyo Koho JP 2008-239543 (Kyorin Pharm.)]. As shown in Scheme 1, the compound I was prepared by dehydration of compound F, and compound J was prepared by deprotection of compound I.

Alternatively, (2S,4S)-4-fluoropyrrolidine-2-carbonitriles compounds I and J were prepared as shown in Scheme 2 according to the literature [WO 03/002533 A2 (Smithkline Beecham)]. Thus, compound A was N-protected in step (xiv), followed by steps (xv) and (xvi), transformation of compound M to compound N (two steps; reaction with di-tert-butyldicarbonate and then with ammonium hydrogen carbonate); then step (xvii) dehydration of compound N with trifluoroacetic anhydride and pyridine, and step (xviii) fluorination of compound O with DAST, giving compound I. N-deprotection of compound I gave compound J.

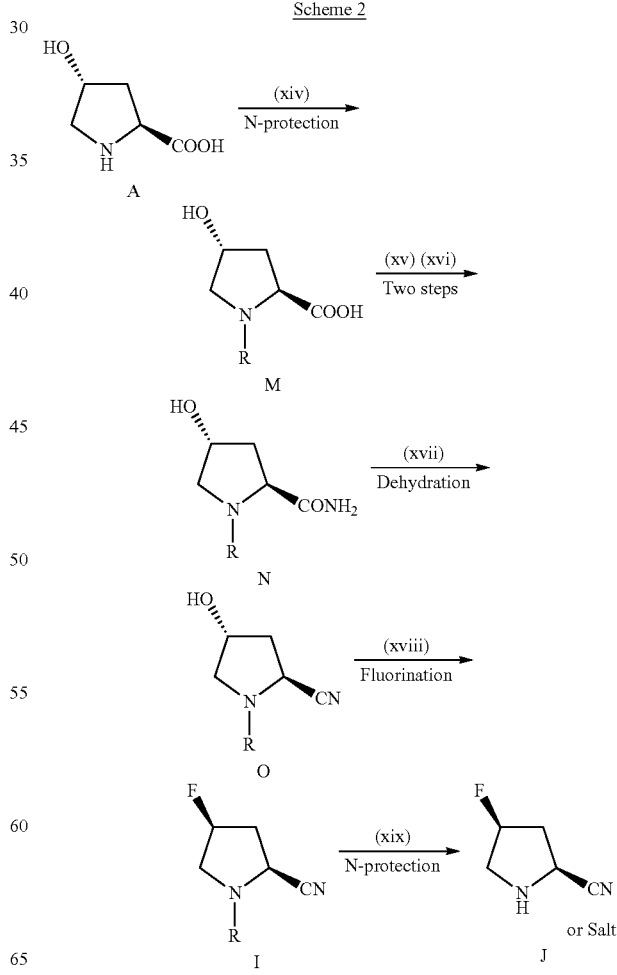

According to the literature [WO 2008/001195 A2 (GlenMark Pharm.)], compound I was also prepared from compound N via step (xx), O-substitution (O-protection). Step (xxi) is a dehydration of compound P with POCl₃, imidazole, and pyridine, and step (xxii) O-deprotection of compound Q with ammonia gas, and finally step (xxiii) fluorination of compound O with DAST, as shown in Scheme 3.

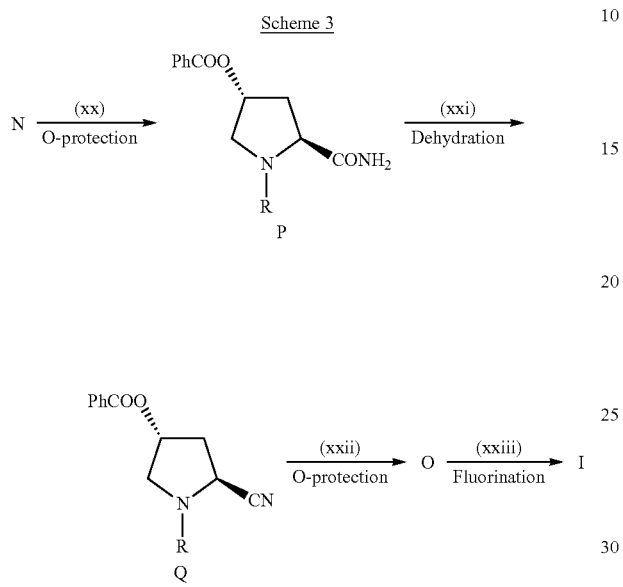

There are a number of significant drawbacks to these conventional methodologies in the production of fluorinated intermediate compounds. These conventional methodologies require a large number of stereospecific chemical transformations for the preparation of the intermediates, which significantly reduces overall yield, thereby increasing cost and time. In addition, these processes required tedious purification steps.

As such, problems with production methods for the fluorinated intermediate compounds herein have made it difficult to prepare useful, highly pure therapeutics in a cost effective and timely fashion. Therefore, there is a need in the art for a methodology which makes it possible to prepare fluorinated intermediates easily and cost effectively. The present invention is directed toward overcoming one or more of the problems discussed above.

As will be more fully described below, the present inventors have developed a stereospecific double fluorination of 4-hydroxypyrrolidine-2-carboxylic acid compounds. Embodiments of the invention significantly decrease the necessary reaction steps, and in addition, attain highly pure products through highly stereospecific reactions. Thus, the compounds and processes of the present invention provide a novel, relatively easy and cost effective method for the preparation of highly pure fluorinated intermediates useful for therapeutics such as DDP IV inhibitors. Embodiments herein provide a significant and unexpected improvement over the state of the art.

SUMMARY OF THE INVENTION

The present invention provides a 4-fluoropyrrolidine-2-carbonyl fluoride compound having a formula (I) as follows;

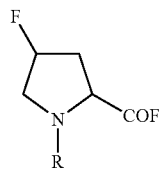

in which R is a substituted or unsubstituted alkoxycarbonyl group having 2 to 35 carbon atoms, a substituted or unsubstituted aryloxycarbonyl group having 7 to 35 carbon atoms, a substituted or unsubstituted acyl group having 1 to 35 carbon atoms, a substituted or unsubstituted alkanesulfonyl group having 1 to 35 carbon atoms, or a substituted or unsubstituted arenesulfonyl group having 6 to 35 carbon atoms, a substituted or unsubstituted alkyl group having 1 to 35 carbon atoms, or a substituted or unsubstituted aryl group having 6 to 35 carbon atoms.

The present invention also provides a useful method for preparing a 4-fluoropyrrolidine-2-carbonyl fluoride compound having a formula (I):

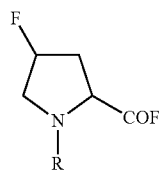

by reacting a 4-hydroxypyrrolidine-2-carboxylic acid compound having a formula (II) with a fluorinating agent.

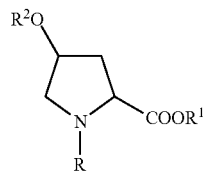

With regard to formula (II), R is the same as described above for formula (I). $R^1$ and $R^2$ each is independently a hydrogen atom or a $SiR^3R^4R^5$ group, in which $R^3$, $R^4$, and $R^5$ each is independently an alkyl group having 1 to 4 carbon atoms, an aralkyl group having 6 to 10 carbon atoms, or an aryl group having 6 to 10 carbon atoms.

The fluorinating agent herein is selected from reagents which can undertake a deoxo-fluorination reaction. In some embodiments, the fluorinating agent is selected from a group consisting of substituted or unsubstituted phenylsulfur trifluorides, substituted (diamino)difluoromethane, substituted α,α-difluoroalkylamines, substituted aminosulfur trifluorides, and sulfur tetrafluoride. It is envisioned that one or more fluorinating agents may be used in combination in the methods as described herein.

In addition, this invention provides N-haloacetyl-4-hydroxypyrrolidine-2-carboxylic acid compounds having a formula (II') as follows:

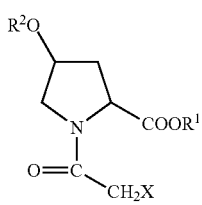

(II')

in which X is a halogen atom, and $R^1$ and $R^2$ are the same as described above.

These and various other features as well as advantages which characterize embodiments of the invention will be apparent from a reading of the following detailed description and a review of the appended claims.

DETAILED DESCRIPTION OF THE INVENTION

The invention provides novel 4-fluoropyrrolidine-2-carbonyl fluoride compounds as useful intermediates for the production of various kinds of therapeutics, such as inhibitors and other like bioactive compounds, and to the methods for preparing them.

Embodiments of the present invention provide useful 4-fluoropyrrolidine-2-carbonyl fluoride compounds, as represented by formula (I):

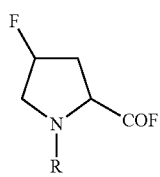

(I)

in which R is a substituted or unsubstituted alkoxycarbonyl group having 2 to 35 carbon atoms, preferably 2 to 25 carbon atoms, more preferably 2 to 15 carbon atoms; a substituted or unsubstituted aryloxycarbonyl group having 7 to 35 carbon atoms, preferably 7 to 25 carbon atoms, more preferably 7 to 15 carbon atoms; a substituted or unsubstituted acyl group having 1 to 35 carbon atoms, preferably 1 to 25 carbon atoms, and more preferably 1 to 15 carbon atoms; a substituted or unsubstituted alkanesulfonyl group having 1 to 35 carbon atoms, preferably 1 to 25 carbon atoms, and more preferably 1 to 15 carbon atoms; a substituted or unsubstituted arenesulfonyl group having 6 to 35 carbon atoms, preferably 6 to 25 carbon atoms, and more preferably 6 to 15 carbon atoms; a substituted or unsubstituted alkyl group having 1 to 35 carbon atoms, preferably 1 to 25 carbon atoms, and more preferably 1 to 15 carbon atoms; or a substituted or unsubstituted aryl group having 6 to 35 carbon atoms, preferably 6 to 25 carbon atoms, and more preferably 6 to 15 carbon atoms.

The term "alkyl" as used herein is linear, branched, or cyclic alkyl. The alkyl part of alkoxycarbonyl or alkanesulfonyl group as used herein is also linear, branched, or cyclic alkyl part. When an acyl group contain an alkyl part, the alkyl part is also linear, branched, or cyclic alkyl part.

The term "substituted alkoxycarbonyl" as used herein means an alkoxycarbonyl moiety having one or more substituents such as a halogen atom, a substituted or unsubstituted aryl group, and/or any other group with or without a heteroatom(s) such as an oxygen atom(s), a nitrogen atom(s), and/or a sulfur atom(s), which does not limit reactions of this invention.

The term "substituted aryloxycarbonyl" as used herein means an aryloxycarbonyl moiety having one or more substituents such as a halogen atom, a substituted or unsubstituted alkyl group, and/or any other group with or without a heteroatom(s) such as an oxygen atom(s), a nitrogen atom(s), and/or a sulfur atom(s), which does not limit reactions of this invention.

The term "substituted acyl" as used herein means an acyl moiety having one or more substituents such as a halogen atom, a substituted or unsubstituted alkyl group, a substituted or unsubstituted aryl group, and/or any other group with or without a heteroatom(s) such as an oxygen atom(s), a nitrogen atom(s), and/or a sulfur atom(s), which does not limit reactions of this invention.

The term "substituted alkanesulfonyl" as used herein means an alkanesulfonyl moiety having one or more substituents such as a halogen atom, a substituted or unsubstituted aryl group, and/or any other group with or without a heteroatom(s) such as an oxygen atom(s), a nitrogen atom(s), and/or a sulfur atom(s), which does not limit reactions of this invention.

The term "substituted arenesulfonyl" as used herein means an arenesulfonyl moiety having one or more substituents such as a halogen atom, a substituted or unsubstituted alkyl group, and/or any other group with or without a heteroatom(s) such as an oxygen atom(s), a nitrogen atom(s), and/or a sulfur atom(s), which does not limit reactions of this invention.

The term "substituted alkyl" as used herein means an alkyl moiety having one or more substituents such as a halogen atom, a substituted or unsubstituted aryl group, and/or any other group with or without a heteroatom(s) such as an oxygen atom(s), a nitrogen atom(s), and/or a sulfur atom(s), which does not limit reactions of this invention.

The term "substituted aryl" as used herein means an aryl moiety having one or more substituents such as a halogen atom, a substituted or unsubstituted alkyl group, and/or any other group with or without a heteroatom(s) such as an oxygen atom(s), a nitrogen atom(s), and/or a sulfur atom(s), which does not limit reactions of this invention.

Preferable examples of a substituted or unsubstituted alkoxycarbonyl group having 2 to 35 carbon atoms include: methoxycarbonyl, ethoxycarbonyl, propoxycarbonyl, isoproxycarbonyl, n-butoxycarbonyl, sec-butoxycarbonyl, isobutoxycarbonyl, tert-butoxycarbonyl, cyclopentyloxycarbonyl, cyclohexyloxycarbonyl, 1-adamantyloxycarbonyl, 2-adamantyloxycarbonyl, benzyloxycarbonyl, 2-phenylethoxycarbonyl, 2-chloroethoxycarbonyl, 2,2,2-trichloroethoxycarbonyl, 2-(trimethylsilyl)ethoxycarbonyl, 1,1-dimethyl-2-bromoethoxycarbonyl, 1,1-dimethyl-2-chloroethoxycarbonyl, 1,1-dimethyl-2,2-dibromoethoxycarbonyl, 1,1-dimethyl-2,2,2-trichloroethoxycarbonyl, 9-fluorenylmethoxycarbonyl, 9-(2,7-dibromo)fluorenylmethoxycarbonyl, 2-chloro-3-indenylmethoxycarbonyl, benz[f]inden-3-ylmethoxycarbonyl, 1,1-dioxobenzo[b]thiophene-2-ylmethoxycarbonyl, 2,7-di-tert-butyl[9-(10,10-dioxo-10,10,10,10-tetrahydrothioxanthyl)methoxycarbonyl, 17-tetrabenzo[a,c,g,i]fluorenylmethoxycarbonyl, and so on.

Preferable examples of a substituted or unsubstituted aryloxycarbonyl group having 7 to 35 carbon atoms include: phenoxycarbonyl, methylphenoxycarbonyl, dimethylphenoxycarbonyl, trimethylphenoxycarbonyl, 2,4,6-tri-tert-butylphenoxycarbonyl, chlorophenoxycarbonyl, bromophenoxycarbonyl, nitrophenoxycarbonyl, pentafluorophenoxycarbonyl, pentachlorophenoxycarbonyl, biphenylyloxycarbonyl, terphenylyloxycarbonyl, and so on.

Preferable examples of a substituted or unsubstituted acyl group having 1 to 35 carbon atoms include: formyl, acetyl, fluoroacetyl, chloroacetyl, bromoacetyl, iodoacetyl, trichloroacetyl, trifluoroacetyl, phenylacetyl, (o-nitrophenyl)acetyl, (o-nitrophenoxy)acetyl, 3-phenylpropionyl, 4-pentenoyl, benzoyl, o-nitrobenzoyl, p-nitrobenzoyl, phenylbenzoyl, diphenylylbenzoyl, and so on.

Preferable examples of a substituted or unsubstituted alkanesulfonyl group having 1 to 35 carbon atoms include: methanesulfonyl, 2-(trimethylsilyl)ethanesulfonyl, benzylsulfonyl, phenacylsulfonyl, tert-butylsulfonyl, trifluoromethanesulfonyl, and so on.

Preferable examples of a substituted or unsubstituted arenesulfonyl group having 6 to 35 carbon atoms include: benzenesulfonyl, toluenesulfonyl, pentamethylbenzenesulfonyl, 2,3,6-trimethyl-4-methoxybenzenesulfonyl, 2,3,5,6-tetramethyl-4-methoxybenzenesulfonyl, 2,4,6-trimethoxybenzenesulfonyl, biphenylsulfonyl, naphthalenesulfonyl, 2-nitrobenzenesulfonyl, 4-nitrobenzensulfonyl, 2,4-dinitrobenzenesulfonyl, 9-anthracenesulfonyl, 4-(4',8'-dimethoxynaphthylmethyl)benzenesulfonyl, and so on.

Preferable examples of a substituted or unsubstituted alkyl group having 1 to 35 carbon atoms include: methyl, ethyl, propyl, isopropyl, n-butyl, sec-butyl, isobutyl, tert-butyl, benzyl, 4-methoxybenzyl, 2,4-dimethoxybenzyl, diphenylmethyl, bis(4-methoxyphenyl)methyl, 5-dibenzosuberyl, 9-fluorenyl, 9-phenylfluorenyl, triphenylmethyl, (4-mthoxyphenyl)diphenylmethyl, allyl, cyanomethyl, [2-(trimethylsilyl)ethoxy]methyl, ferrocenylmethyl, 3-acetoxypropyl, and so on.

Preferable examples of a substituted or unsubstituted aryl group having 6 to 35 carbon atoms include: phenyl, 2-tolyl, 3-tolyl, 4-tolyl, fluorophenyl, chlorophenyl, bromophenyl, iodophenyl, 2-nitrophenyl, 4-nitrophenyl, 2,4-dinitrophenyl, pentachlorophenyl, pentafluorophenyl, diphenylyl, terphenylyl, and so on.

Among R groups of formula (I) described above, the substituted or unsubstituted alkoxycarbonyl group and the substituted or unsubstituted acyl group are preferable because of relative availability of starting materials and high fluorination yields and valuable application of the compounds of formula (I).

Compounds of the invention may comprise two or more chiral centers so that the compounds may exist as stereoisomers, including diasteroisomers, enantiomers, and rotamers (rotational isomers). All such compounds are within the scope of the present invention, including all such stereoisomers, and mixtures thereof, including racemates.

Optical activity and ability to measure optical activity are terms known in the art and their use herein is consistent with normal use in the art. The R,S system (Cahn-Ingold-Prelog or CIP system) is used to provide configuration of compounds herein and is also known in the art.

Preferable examples of compounds of formula (I) in accordance with the present invention include: (2S,4S)—N-(9-fluorenylmethoxycarbonyl)-4-fluoropyrrolidine-2-carbonyl fluoride, (2R,4R)—N-(9-fluorenylmethoxycarbonyl)-4-fluoropyrrolidine-2-carbonyl fluoride, (2S,4R)—N-(9-fluorenylmethoxycarbonyl)-4-fluoropyrrolidine-2-carbonyl fluoride, (2R,4S)—N-(9-fluorenylmethoxycarbonyl)-4-fluoropyrrolidine-2-carbonyl fluoride, racemic N-(9-fluorenylmethoxycarbonyl)-cis-4-fluoropyrrolidine-2-carbonyl fluoride, racemic N-(9-fluorenylmethoxycarbonyl)-trans-4-fluoropyrrolidine-2-carbonyl fluoride, (2S,4S)—N-(benzyloxycarbonyl)-4-fluoropyrrolidine-2-carbonyl fluoride, (2R,4R)—N-(benzyloxycarbonyl)-4-fluoropyrrolidine-2-carbonyl fluoride, (2S,4R)—N-(benzyloxycarbonyl)-4-fluoropyrrolidine-2-carbonyl fluoride, (2R,4S)—N-(benzyloxycarbonyl)-4-fluoropyrrolidine-2-carbonyl fluoride, racemic N-(benzyloxycarbonyl)-cis-4-fluoropyrrolidine-2-carbonyl fluoride, racemic N-(benzyloxycarbonyl)-trans-4-fluoropyrrolidine-2-carbonyl fluoride, (2S,4S)—N-(tert-butoxycarbonyl)-4-fluoropyrrolidine-2-carbonyl fluoride, (2R,4R)—N-(tert-butoxycarbonyl)-4-fluoropyrrolidine-2-carbonyl fluoride, (2S,4R)—N-(tert-butoxycarbonyl)-4-fluoropyrrolidine-2-carbonyl fluoride, (2R,4S)—N-(tert-butoxycarbonyl)-4-fluoropyrrolidine-2-carbonyl fluoride, racemic N-(tert-butoxycarbonyl)-cis-4-fluoropyrrolidine-2-carbonyl fluoride, racemic N-(tert-butoxycarbonyl)-trans-4-fluoropyrrolidine-2-carbonyl fluoride, (2S,4S)—N-chloroacetyl-4-fluoropyrrolidine-2-carbonyl fluoride, (2R,4R)—N-chloroacetyl-4-fluoropyrrolidine-2-carbonyl fluoride, (2S,4R)—N-chloroacetyl-4-fluoropyrrolidine-2-carbonyl fluoride, (2R,4S)—N-chloroacetyl-4-fluoropyrrolidine-2-carbonyl fluoride, racemic N-chloroacetyl-cis-4-fluoropyrrolidine-2-carbonyl fluoride, racemic N-chloroacetyl-trans-4-fluoropyrrolidine-2-carbonyl fluoride, (2S,4S)—N-bromoacetyl-4-fluoropyrrolidine-2-carbonyl fluoride, (2R,4R)—N-bromoacetyl-4-fluoropyrrolidine-2-carbonyl fluoride, (2S,4R)—N-bromoacetyl-4-fluoropyrrolidine-2-carbonyl fluoride, (2R,4S)—N-bromoacetyl-4-fluoropyrrolidine-2-carbonyl fluoride, racemic N-bromoacetyl-cis-4-fluoropyrrolidine-2-carbonyl fluoride, racemic N-bromoacetyl-trans-4-fluoropyrrolidine-2-carbonyl fluoride, (2S,4S)—N-iodooacetyl-4-fluoropyrrolidine-2-carbonyl fluoride, (2R,4R)—N-iodoacetyl-4-fluoropyrrolidine-2-carbonyl fluoride, (2S,4R)—N-iodoacetyl-4-fluoropyrrolidine-2-carbonyl fluoride, (2R,4S)—N-iodoacetyl-4-fluoropyrrolidine-2-carbonyl fluoride, racemic N-iodoacetyl-cis-4-fluoropyrrolidine-2-carbonyl fluoride, racemic N-iodoacetyl-trans-4-fluoropyrrolidine-2-carbonyl fluoride, and other like compounds.

More preferable examples of formula (I) in accordance with the present invention include: (2S,4S)—N-(9-fluorenylmethoxycarbonyl)-4-fluoropyrrolidine-2-carbonyl fluoride, (2S,4R)—N-(9-fluorenylmethoxycarbonyl)-4-fluoropyrrolidine-2-carbonyl fluoride, (2S,4S)—N-(benzyloxycarbonyl)-4-fluoropyrrolidine-2-carbonyl fluoride, (2S,4R)—N-(benzyloxycarbonyl)-4-fluoropyrrolidine-2-carbonyl fluoride, (2S,4S)—N-(tert-butoxycarbonyl)-4-fluoropyrrolidine-2-carbonyl fluoride, (2S,4R)—N-(tert-butoxycarbonyl)-4-fluoropyrrolidine-2-carbonyl fluoride, (2S,4S)—N-chloroacetyl-4-fluoropyrrolidine-2-carbonyl fluoride, (2S,4R)—N-chloroacetyl-4-fluoropyrrolidine-2-carbonyl fluoride, (2S,4S)—N-bromoacetyl-4-fluoropyrrolidine-2-carbonyl fluoride, (2S,4R)—N-bromoacetyl-4-fluoropyrrolidine-2-carbonyl fluoride.

Furthermore preferable examples of formula (I) in accordance with the present invention include: (2S,4S)—N-(9-fluorenylmethoxycarbonyl)-4-fluoropyrrolidine-2-carbonyl fluoride, (2S,4S)—N-(benzyloxycarbonyl)-4-fluoropyrrolidine-2-carbonyl fluoride, (2S,4S)—N-(tert-butoxycarbonyl)-4-fluoropyrrolidine-2-carbonyl fluoride, and (2S,4S)—N-chloroacetyl-4-fluoropyrrolidine-2-carbonyl fluoride.

Embodiments of the present invention provide a method (Scheme 4; Process I) for preparing 4-fluoropyrrolidine-2-carbonyl fluoride compound having a formula (I), which comprises reacting 4-hydroxypyrrolidine-2-carboxylic acid compound having a formula (II) with a fluorinating agent:

Scheme 4; Process I

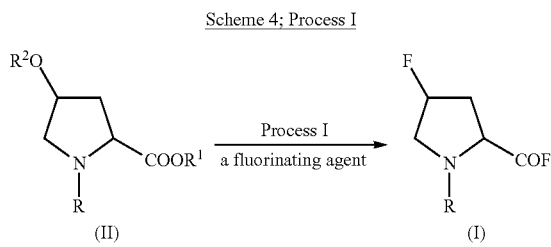

For the compounds represented by formulas (I) and (II), R is the same as described above. $R^1$ and $R^2$ each is independently a hydrogen atom or a $SiR^3R^4R^5$ group, in which $R^3$, $R^4$, and $R^5$ each is independently an alkyl group having 1 to 4 carbon atoms, an aralkyl group having 6 to 10 carbon atoms, or an aryl group having 6 to 10 carbon atoms.

Examples of alkyl groups for $R^3$, $R^4$, or $R^5$ include methyl, ethyl, n-propyl, isopropyl, n-butyl, sec-butyl, isobutyl, tert-butyl, and so on. Examples of aralkyl groups for $R^3$, $R^4$, or $R^5$ include benzyl, methylbenzyl, 2-phenylethyl, and so on. Examples of aryl groups for $R^3$, $R^4$, or $R^5$ include phenyl, tolyl, ethylphenyl, butylphenyl, chlorophenyl, and so on.

Process I

The starting materials, 4-hydroxypyrrolidine-2-carboxylic acid compounds having formula (II), are commercially available or can be prepared in accordance with understood principles of synthetic chemistry.

Illustrative 4-hydroxypyrrolidne-2-carboxylic acid compounds, as presented by formula (II), used in Process I, include: (2S,4R)—N-(9-fluorenylmethoxycarbonyl)-4-hydroxypyrrolidine-2-carboxylic acid [called as N-Fmoc-trans-4-hydroxy-L-proline], (2R,4S)—N-(9-fluorenylmethoxycarbonyl)-4-hydroxypyrrolidine-2-carboxylic acid [N-Fmoc-trans-4-hydroxy-D-proline], (2S,4S)—N-(9-fluorenylmethoxycarbonyl)-4-hydroxypyrrolidine-2-carboxylic acid [N-Fmoc-cis-4-hydroxy-L-proline], (2R,4R)—N-(9-fluorenylmethoxycarbonyl)-4-hydroxypyrrolidine-2-carboxylic acid [N-Fmoc-cis-4-hydroxy-D-proline], racemic N-(9-fluorenylmethoxycarbonyl)-trans-4-hydroxypyrrolidine-2-carboxylic acid [racemic N-Fmoc-trans-4-hydroxyproline], racemic N-(9-fluorenylmethoxycarbonyl)-cis-4-hydroxypyrrolidine-2-carboxylic acid [racemic N-Fmoc-cis-4-hydroxyproline], (2S,4R)—N-(benzyloxycarbonyl)-4-hydroxypyrrolidine-2-carboxylic acid [N-Cbz-trans-4-hydroxy-L-proline], (2R,4S)—N-(9-benzyloxycarbonyl)-4-hydroxypyrrolidine-2-carboxylic acid [N-Cbz-trans-4-hydroxy-D-proline], (2S,4S)—N-(benzyloxycarbonyl)-4-hydroxypyrrolidine-2-carboxylic acid [N-Cbz-cis-4-hydroxy-L-proline], (2R,4R)—N-(benzyloxycarbonyl)-4-hydroxypyrrolidine-2-carboxylic acid [N-Cbz-cis-4-hydroxy-D-proline], racemic N-(benzyloxycarbonyl)-trans-4-hydroxypyrrolidine-2-carboxylic acid [racemic N-Cbz-trans-4-hydroxyproline], racemic N-(benzyloxycarbonyl)-cis-4-hydroxypyrrolidine-2-carboxylic acid [racemic N-Cbz-cis-4-hydroxyproline], (2S,4R)—N-(tert-butoxycarbonyl)-4-hydroxypyrrolidine-2-carboxylic acid [N-Boc-trans-4-hydroxy-L-proline], (2R,4S)—N-(tert-butoxycarbonyl)-4-hydroxypyrrolidine-2-carboxylic acid [N-Boc-trans-4-hydroxy-D-proline], (2S,4S)—N-(tert-butoxycarbonyl)-4-hydroxypyrrolidine-2-carboxylic acid [N-Boc-cis-4-hydroxy-L-proline], (2R,4R)—N-(tert-butoxycarbonyl)-4-hydroxypyrrolidine-2-carboxylic acid [N-Boc-cis-4-hydroxy-D-proline], racemic N-(tert-butoxycarbonyl)-trans-4-hydroxypyrrolidine-2-carboxylic acid [racemic N-Boc-trans-4-hydroxyproline], racemic N-(tert-butoxycarbonyl)-cis-4-hydroxypyrrolidine-2-carboxylic acid [racemic N-Boc-cis-4-hydroxyproline], (2S,4R)—N-chloroacetyl-4-hydroxypyrrolidine-2-carboxylic acid [N-chloroacetyl-trans-4-hydroxy-L-proline], trimethylsilyl (2S,4R)—N-chloroacetyl-4-(trimethylsilyloxy)pyrrolidine-2-carboxylate, (2S,4R)—N-chloroacetyl-4-(trimethylsilyloxy)pyrrolidine-2-carboxylic acid, (2R,4S)—N-chloroacetyl-4-hydroxypyrrolidine-2-carboxylic acid [N-chloroacetyl-trans-4-hydroxy-D-proline], (2S,4S)—N-chloroacetyl-4-hydroxypyrrolidine-2-carboxylic acid [N-chloroacetyl-cis-4-hydroxy-L-proline], (2R,4R)—N-chloroacetyl-4-hydroxypyrrolidine-2-carboxylic acid [N-chloroacetyl-cis-4-hydroxy-D-proline], racemic N-chloroacetyl-trans-4-hydroxypyrrolidine-2-carboxylic acid [racemic N-chloroacetyl-trans-4-hydroxyproline], racemic N-chloroacetyl-cis-4-hydroxypyrrolidine-2-carboxylic acid [racemic N-chloroaceyl-cis-4-hydroxyproline], (2S,4R)—N-bromoacetyl-4-hydroxypyrrolidine-2-carboxylic acid [N-bromoacetyl-trans-4-hydroxy-L-proline], trimethylsilyl (2S,4R)—N-bromoacetyl-4-(trimethylsilyloxy)pyrrolidine-2-carboxylate, (2S,4R)—N-bromoacetyl-4-(trimethylsilyloxy)pyrrolidine-2-carboxylic acid, (2R,4S)—N-bromoacetyl-4-hydroxypyrrolidine-2-carboxylic acid [N-bromoacetyl-trans-4-hydroxy-D-proline], (2S,4S)—N-bromoaceyl-4-hydroxypyrrolidine-2-carboxylic acid [N-bromoacetyl-cis-4-hydroxy-L-proline], (2R,4R)—N-bromoacetyl-4-hydroxypyrrolidine-2-carboxylic acid [N-bromoacetyl-cis-4-hydroxy-D-proline], racemic N-bromoaceyl-trans-4-hydroxypyrrolidine-2-carboxylic acid [racemic N-bromoacetyl-trans-4-hydroxyproline], racemic N-bromoaceyl-cis-4-hydroxypyrrolidine-2-carboxylic acid [racemic N-bromoaceyl-cis-4-hydroxyproline], (2S,4R)—N-iodoacetyl-4-hydroxypyrrolidine-2-carboxylic acid [N-iodoacetyl-trans-4-hydroxy-L-proline], trimethylsilyl (2S,4R)—N-iodoacetyl-4-(trimethylsilyloxy)pyrrolidine-2-carboxylate, (2S,4R)—N-iodoacetyl-4-(trimethylsilyloxy)pyrrolidine-2-carboxylic acid, (2R,4S)—N-iodoacetyl-4-hydroxypyrrolidine-2-carboxylic acid [N-iodoacetyl-trans-4-hydroxy-D-proline], (2S,4S)—N-iodoaceyl-4-hydroxypyrrolidine-2-carboxylic acid [N-iodoacetyl-cis-4-hydroxy-L-proline], (2R,4R)—N-iodoacetyl-4-hydroxypyrrolidine-2-carboxylic acid [N-iodoacetyl-cis-4-hydroxy-D-proline], racemic N-iodoaceyl-trans-4-hydroxypyrrolidine-2-carboxylic acid [racemic N-iodoacetyl-trans-4-hydroxyproline], racemic N-iodoacetyl-cis-4-hydroxypyrrolidine-2-carboxylic acid [racemic N-iodoaceyl-cis-4-hydroxyproline], and other like compounds.

Fluorinating agents herein are reagents that undertake a deoxo-fluorination reaction.

The term "deoxo-fluorination reaction" is the fluorination reaction in which an oxygen(s) or an oxygen-containing group(s) in a molecule is transformed to a fluorine atom(s). In the reaction of the present invention, each of a hydroxyl group (OH) or a $OSiR^3R^4R^5$ group at 4-postion and a OH part of a carboxylic acid or a $OSiR^3R^4R^5$ part of a carboxylate of the molecule (formula (II)) is transformed to a fluorine atom.

The fluorinating agent is preferably selected from a group consisting of substituted or unsubstituted phenylsulfur trifluorides, substituted (diamino)difluoromethane, substituted α,α-difluoroalkylamines, substituted aminosulfur trifluorides, and sulfur tetrafluoride.

The substituted or unsubstituted phenylsulfur trifluorides have a formula (III):

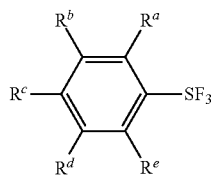

(III)

in which $R^a$, $R^b$, $R^c$, $R^d$, and $R^e$ each is independently a hydrogen atom, a halogen atom, a substituted or unsubstituted alkyl group having 1 to 10 carbon atoms, a nitro group, or a cyano group.

Substituted or unsubstituted phenylsulfur trifluorides have high thermal stability and, in particular, substituted phenylsulfur trifluorides have ease of handling (see U.S. Pat. No. 7,381,846 B2, incorporated herein by reference).

Illustrative substituted or unsubstituted phenylsulfur trifluorides, as represented by formula (III), used in Process I, can be prepared as described in the literature [see J. Am. Chem. Soc., Vol. 82 (1962), pp. 3064-3072; Synthetic Communications, Vol. 33 (2003), pp. 2505-2509; U.S. Pat. No. 7,265,247 B1; and U.S. Pat. No. 7,381,846 B2, each of which is incorporated by reference in its entirety]. Alternatively, substituted or unsubstituted phenylsulfur trifluorides can be prepared from a substituted or unsubstituted phenylsulfur halotetrafluoride with a reducing substance (see U.S. Patent Application No. 61/041,415, incorporated by reference in its entirety). Note that substituted or unsubstituted phenylsulfur trifluorides prepared from substituted or unsubstituted phenylsulfur halotetrafluorides may be used without further purification.

The substituted or unsubstituted phenylsulfur trifluorides are exemplified by, but are not limited to, phenylsulfur trifluoride, each isomer of methylphenylsulfur trifluoride, each isomer of dimethylphenylsulfur trifluoride, each isomer of trimethylphenylsulfur trifluoride, each isomer of ethylphenylsulfur trifluoride, each isomer of (n-propyl)phenylsulfur trifluoride, each isomer of isopropylphenylsulfur trifluoride, each isomer of (n-butyl)phenylsulfur trifluoride, each isomer of isobutylphenylsulfur trifluoride, each isomer of (sec-butyl) phenylsulfur trifluoride, each isomer of (tert-butyl)phenylsulfur trifluoride, each isomer of di(isopropyl)phenylsulfur trifluoride, each isomer of tri(isopropyl)phenylsulfur trifluoride, each isomer of (tert-butyl)dimethylphenylsulfur trifluoride, each isomer of (tert-butyl)(chloro)dimethylphenylsulfur trifluoride, each isomer of (tert-butyl)(dichloro)dimethylphenylsulfur trifluoride, each isomer of (methoxymethyl)phenylsulfur trifluoride, each isomer of bis(methoxymethyl) phenylsulfur trifluoride, each isomer of bis(methoxymethyl)-tert-butylphenylsulfur trifluoride, each isomer of bis (ethoxymethyl)-(tert-butyl)phenylsulfur trifluoride, each isomer of bis(isopropoxymethyl)-(tert-butyl)phenylsulfur trifluoride, each isomer of fluorophenylsulfur trifluoride, each isomer of chlorophenylsulfur trifluoride, each isomer of bromophenylsulfur trifluoride, each isomer of iodophenylsulfur trifluoride, each isomer of difluorophenylsulfur trifluoride, each isomer of trifluorophenylsulfur trifluoride, each isomer of tetrafluorophenylsulfur trifluoride, pentafluorophenylsulfur trifluoride, each isomer of dichlorophenylsulfur trifluoride, each isomer of dibromophenylsulfur trifluoride, each isomer of chlorofluorophenylsulfur trifluoride, each isomer of bromofluorophenylsulfur trifluoride, each isomer of chloro(methyl)phenylsulfur trifluoride, each isomer of chloro (dimethyl)phenylsulfur trifluoride, each isomer of nitrophenylsulfur trifluoride, each isomer of dinitrophenylsulfur trifluoride, each isomer of cyanophenylsulfur trifluoride, and other like compounds.

Among these substituted or unsubstituted phenylsulfur trifluorides, phenylsulfur trifluoride, 4-methylphenylsulfur trifluoride, 2,4-dimethylphenylsulfur trifluoride, 2,5-dimethylphenylsulfur trifluoride, 2,4,6-trimethylphenylsulfur trifluoride, 4-(tert-butyl)phenylsulfur trifluoride, 2,4,6-tri (isopropyl)phenylsulfur trifluoride, 4-(tert-butyl)-2,6-dimethylphenylsulfur trifluoride, 4-(tert-butyl)-3-chloro-2,6-dimethylphenylsulfur trifluoride, 2,6-bis(methoxymethyl) phenylsulfur trifluoride, 2,6-bis(ethoxymethyl)phenylsulfur trifluoride, 2,6-bis(methoxymethyl)-4-tert-butylphenylsulfur trifluoride, 2,6-bis(ethoxymethyl)-4-(tert-butyl)phenylsulfur trifluoride, 4-fluorophenylsulfur trifluoride, and 4-chlorophenylsulfur trifluoride are preferable.

More preferable still are phenylsulfur trifluoride, 4-methylphenylsulfur trifluoride, 4-(tert-butyl)phenylsulfur trifluoride, 4-(tert-butyl)-2,6-dimethylphenylsulfur trifluoride, 2,6-bis(methoxymethyl)phenylsulfur trifluoride, 2,6-bis (methoxymethyl)-4-(tert-butyl)phenylsulfur trifluoride, 4-fluorophenylsulfur trifluoride, and 4-chlorophenylsulfur trifluoride.

Furthermore preferable are phenylsulfur trifluoride, 4-methylphenylsulfur trifluoride, 4-(tert-butyl)phenylsulfur trifluoride, 4-(tert-butyl)-2,6-dimethylphenylsulfur trifluoride, 4-fluorophenylsulfur trifluoride, and 4-chlorophenylsulfur trifluoride.

The most preferable is 4-(tert-butyl)-2,6-dimethylphenylsulfur trifluoride due to its relative availability, safety, ease of handling, and product yield.

Examples of substituted (diamino)difluoromethanes include: 2,2-difluoro-1,3-dimethylimidazolidine, 2,2-difluoro-1,3-di(n-butyl)imidazolidine, bis(N,N-dimethylamino)difluoromethane, bis[N,N-di(n-butyl)amino]difluoromethane, and other like compounds. Among the (diamino) difluoromethanes, 2,2-difluoro-1,3-dimethylimidazolidine is preferable due to relative availability.

Examples of substituted α,α-difluoroalkylamines include: $ClCHFCF_2N(CH_2CH_3)_2$ (Yarovenko reagent), $CF_3CHFCF_2N(CH_2CH_3)_2$ (Ishikawa reagent), $CF_2HCF_2N(CH_3)_2$, $CF_2HCF_2N(CH_2CH_3)_2$, N,N-diethyl-(α,α-difluoro) benzylamine $[C_6H_5CF_2N(CH_2CH_3)_2]$, N,N-diethyl-α,α-difluoro(m-methylbenzyl)amine $[m-CH_3C_6H_4CF_2N(CH_2CH_3)_2]$, and other like compounds. Among these, Yarovenko reagent, Ishikawa reagent, and $CF_2HCF_2N(CH_3)_2$ are preferable due to availability.

Examples of substituted aminosulfur trifluorides include: dimethylaminosulfur trifluoride, diethylaminosulfur trifluoride (DAST), morpholinosulfur trifluoride, bis(2-methoxyethyl)aminosulfur trifluoride (Deoxo-Fluor™ reagent), and other like compounds. Among these, dimethylaminosulfur trifluoride, DAST and Deoxo-Fluor™ are preferable due to availability.

Among these, the substituted or unsubstituted phenylsulfur trifluorides, substituted (diamino)difluoromethane, and substituted α,α-difluoroalkylamines are more preferable due to yield and cost, and the phenylsulfur trifluorides are furthermore preferable due to high safety and yield. Among the phenylsulfur trifluorides, 4-(tert-butyl)-2,6-dimethylphenylsulfur trifluoride is most preferable due to high yield and ease of handling.

The reaction of Process I can be carried out with addition of hydrogen fluoride (HF) or a mixture of hydrogen fluoride and an organic compound(s) since hydrogen fluoride or a mixture of hydrogen fluoride and an organic compound(s) may accelerate the fluorination reaction.

In one embodiment, the hydrogen fluoride is in situ generated by addition of a necessary amount of water or an alcohol such as methanol, ethanol, propanol, butanol, and so on. The water or alcohol is added into the reaction mixture, since a fluorinating agent reacts with water or an alcohol to generate hydrogen fluoride, however, this in situ generation method of hydrogen fluoride requires the fluorinating agent be consumed at equimolar amounts of water or alcohol.

Examples of a mixture of hydrogen fluoride and an organic compound(s) include a mixture of hydrogen fluoride and pyridine, a mixture of hydrogen fluoride and triethylamine, a mixture of hydrogen fluoride and dimethyl ether, a mixture of hydrogen fluoride and diethyl ether, a mixture of hydrogen fluoride and urea, and so on. Among them, a mixture of hydrogen fluoride and pyridine and a mixture of hydrogen fluoride and triethylamine are preferable, and furthermore, a mixture of about 70 wt % hydrogen fluoride and about 30 wt % pyridine and a 3:1 molar ratio mixture of hydrogen fluoride and triethylamine ($Et_3N.3HF$) are more preferable due to commercial availability. The amount of hydrogen fluoride used or a mixture of hydrogen fluoride and an amine(s) is selected from a catalytic amount to a large excess.

When the starting material and/or the product are sensitive to acid conditions, the reaction of Process I may be carried out in the presence of a base. Examples of a base herein include metal fluorides such as sodium fluoride, potassium fluoride, cesium fluoride, and so on; amines such as pyridine, chloropyridine, fluoropyridine, methylpyridine, dimethylpyridine, trimethylpyridine, triethylamine, and so on; carbonates such as sodium carbonate, sodium bicarbonate, potassium carbonate, potassium bicarbonate, and so on. Among these bases, metal fluorides are preferable because of the relative high yield of the product.

Embodiments of Process I can be carried out in the presence of one or more solvents. The use of solvent is preferable for mild and efficient reactions. However, some embodiments herein are performed in the absence of solvent. Preferable solvents will not substantially react with the starting materials and reagents, the intermediates, and/or the final products. Suitable solvents include, but are not limited to, alkanes, halocarbons, ethers, nitriles, aromatics, nitroalkanes, and so on, and mixtures thereof. Example alkanes include normal, branched, cyclic isomers of pentane, hexane, heptane, octane, nonane, decane, dodecane, undecane, and other like compounds. Illustrative halocarbons include dichloromethane, chloroform, carbon tetrachloride, dichloroethane, trichloroethane, tetrachloroethane, trichlorotrifluoroethane, chlorobenzene, dichlorobenzene, hexafluorobenzene, and benzotrifluoride; normal, branched, cyclic isomers of perfluoropentane, perfluorohexane, perfluoroheptane, perfluorooctane, perfluorononane, and perfluorodecane; perfluorodecalin; and other like compounds. Illustrative ethers include diethyl ether, dipropyl ether, di(isopropyl)ether, dibutyl ether, tert-butyl methyl ether, dioxane, glyme (1,2-dimethoxyethane), diglyme, triglyme, and other like compounds. Illustrative nitriles include acetonitrile, propionitrile, and other like compounds. Illustrative aromatics include benzene, toluene, xylene, and other like compounds. Illustrative nitroalkanes include nitromethane, nitroethane, and other like compounds.

In order to obtain good yields of product in Process I, the reaction temperature can preferably be selected in the range of about −100° C. to about +150° C. More preferably, the reaction temperature can be selected in the range of about −80° C. to about +100° C. Furthermore preferably, the reaction temperature can be selected in the range of about −80° C. to about +70° C.

Reaction conditions of Process I are optimized to obtain economically good yields of product. Where a fluorinating agent, used in Process I, can transform a OH group to a fluorine atom, from about 2 mol or more, preferably about 2 mol to about 5 mol, more preferably, from about 2 mol to about 3 mol of a fluorinating agent are combined with about 1 mol of a 4-hydroxypyrrolidine-2-carboxylic acid compound (formula (II)) to obtain a good yield of 4-fluoropyrrolidine-2-carbonyl fluoride compound (formula (I)).

Where a fluorinating agent used in Process I can transform n (OH groups) to n fluorine atoms, from about 2/n mol or more, preferably about 2/n mol to about 5/n mol, more preferably, from about 2/n mol to about 3/n mol of a fluorinating agent are combined with about 1 mol of a 4-hydroxypyrrolidine-2-carboxylic acid compound (formula (II)) to obtain a good yield of 4-fluoropyrrolidine-2-carbonyl fluoride compound (formula (I)).

Note that the reaction time for Process I varies dependent upon reaction temperature, and the types and amounts of substrates, reagents, and solvents. As such, reaction time is generally determined as the amount of time required to complete a particular reaction, but can be from about 0.1 h to about a few weeks, preferably, within a week.

In another embodiment, 4-fluoropyrrolidine-2-carbonyl fluoride compound (formula (I)) is synthesized by fluorination of a N-substituted 4-fluoropyrrolidine-2-carboxylic acid with a fluorinating agent (see Examples 11~13).

The present invention also provides a new compound, N-haloacetyl-4-hydroxypyrrolidine-2-carboxylic acid compound, having a formula (II') as follows:

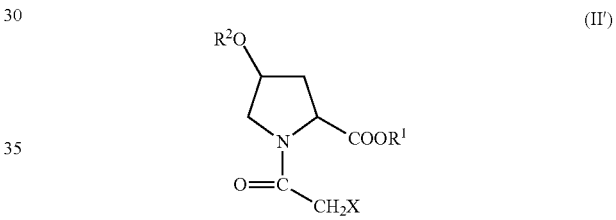

(II')

in which X is a halogen atom; and $R^1$ and $R^2$ are the same as described above.

The halogen atom in formula (II') is a fluorine atom, chlorine atom, bromine atom, or iodine atom. A chlorine atom, bromine atom, or iodine atom is more preferable. A chlorine atom or bromine atom is furthermore preferable.

The compounds of formula (II') of the invention may comprise two or more chiral centers so that the compounds may exist as stereoisomers, including diastereoisomers, enantiomers, and rotamers (rotational isomers). All such compounds are within the scope of the present invention, including all such stereoisomers, and mixtures thereof, including racemates.

Optical activity and ability to measure optical activity are terms known in the art and their use herein is consistent with normal use in the art. The R,S system (Cahn-Ingold-Prelog or CIP system) is used to provide configuration of compounds herein and is also known in the art.

The N-haloacetyl-4-hydroxypyrrolidine-2-carboxylic acid compound having a formula (II') is a useful intermediate for the preparation of 4-fluoropyrrolidine-2-carbonyl fluoride compounds as presented by formula (I) (see, for example, Example 10).

The N-haloacetyl-4-hydroxypyrrolidine-2-carboxylic acid compound having a formula (II') can be prepared by the following methods: (1) reaction of trimethylsilyl N-(trimethylsilyl)-4-(trimethylsilyloxy)pyrrolidine-2-carboxylate with haloacetyl fluoride (see Examples 24 and 27), if needed, followed by desilylation (see Example 25); and/or (2) reaction of trimethylsilyl 4-(trimethylsilyloxy)pyrrolidine-2-carboxylate with a haloacetyl halide (see Example 26, step 1), if needed, followed by desilylation (see Example 26, step 2).

Preferable examples of the compounds of formula (II') of the present invention include: (2S,4S)—N-(chloroacetyl)-4-hydroxypyrrolidine-2-carboxylic acid, (2R,4R)—N-(chloroaceyl)-4-hydroxypyrrolidine-2-carboxylic acid, (2S,4R)—N-(chloroacetyl)-4-hydroxypyrrolidine-2-carboxylic acid, (2R,4S)—N-(chloroacetyl)-4-hydroxypyrrolidine-2-carboxylic acid, racemic N-(chloroacetyl)-cis-4-hydroxypyrrolidine-2-carboxylic acid, racemic N-(chloroacetyl)-trans-4-hydroxypyrrolidine-2-carboxylic acid, trimethylsilyl (2S,4S)—N-(choloroacetyl)-4-(trimethylsilyloxy)pyrrolidine-2-carboxylate, trimethylsilyl (2S,4S)—N-(chloroacetyl)-4-hydroxypyrrolidine-2-carboxylate, (2S,4S)—N-(choloroacetyl)-4-(trimethylsilyloxy)pyrrolidine-2-carboxylic acid, trimethylsilyl (2R,4R)—N-(chloroacetyl)-4-(trimethylsilyloxy)pyrrolidine-2-carboxylate, trimethylsilyl (2S,4R)—N-(chloroacetyl)-4-(trimethylsilyloxy)pyrrolidine-2-carboxylate, (2S,4R)—N-(choloroacetyl)-4-(trimethylsilyloxy)pyrrolidine-2-carboxylic acid, trimethylsilyl (2S,4R)—N-(chloroacetyl)-4-hydroxypyrrolidine-2-carboxylate, triethylsilyl (2S,4R)—N-(chloroacetyl)-4-(triethylsilyloxy)pyrrolidine-2-carboxylate, triethylsilyl (2S,4R)—N-(chloroacetyl)-4-hydroxypyrrolidine-2-carboxylate, (2S,4R)—N-(chloroacetyl)-4-(triethylsilyloxy)pyrrolidine-2-carboxylic acid, trimethylsilyl (2R,4S)—N-(chloroacetyl)-4-(trimethylsilyloxy)pyrrolidine-2-carboxylate, (2R,4S)—N-(chloroacetyl)-4-(trimethylsilyloxy)pyrrolidine-2-carboxylic acid, racemic trimethylsilyl N-(chloroacetyl)-cis-4-(trimethylsilyloxy)pyrrolidine-2-carboxylate, racemic N-(chloroacetyl)-cis-4-(trimethylsilyloxy)pyrrolidine-2-carboxylic acid, racemic trimethylsilyl N-(chloroacetyl)-trans-4-(trimethylsilyloxy)pyrrolidine-2-carboxylate, racemic N-(chloroacetyl)-trans-4-(trimethylsilyloxy)pyrrolidine-2-carboxylic acid, (2S,4S)—N-(bromoacetyl)-4-hydroxypyrrolidine-2-carboxylic acid, (2R,4R)—N-(bromoaceyl)-4-hydroxypyrrolidine-2-carboxylic acid, (2S,4R)—N-(bromoacetyl)-4-hydroxypyrrolidine-2-carboxylic acid, (2R,4S)—N-(bromoacetyl)-4-hydroxypyrrolidine-2-carboxylic acid, racemic N-(bromoacetyl)-cis-4-hydroxypyrrolidine-2-carboxylic acid, racemic N-(bromoacetyl)-trans-4-hydroxypyrrolidine-2-carboxylic acid, trimethylsilyl (2S,4S)—N-(bromoacetyl)-4-(trimethylsilyloxy)pyrrolidine-2-carboxylate, trimethylsilyl (2R,4R)—N-(bromoaceyl)-4-(trimethylsilyloxy)pyrrolidine-2-carboxylate, trimethylsilyl (2S,4R)—N-(bromoacetyl)-4-(trimethylsilyloxy)pyrrolidine-2-carboxylate, (2S,4R)—N-(bromoacetyl)-4-(trimethylsilyloxy)pyrrolidine-2-carboxylic acid, trimethylsilyl (2S,4R)—N-(bromoacetyl)-4-hydroxypyrrolidine-2-carboxylate, triethylsilyl (2S,4R)—N-(bromoacetyl)-4-(triethylsilyloxy)pyrrolidine-2-carboxylate, (2S,4R)—N-(bromoacetyl)-4-(triethylsilyloxy)pyrrolidine-2-carboxylic acid, racemic trimethylsilyl N-(bromoacetyl)-cis-4-(trimethylsilyloxy)pyrrolidine-2-carboxylate, racemic trimethylsilyl N-(bromoacetyl)-trans-4-(trimethylsilyloxy)pyrrolidine-2-carboxylate, (2S,4S)—N-(iodoacetyl)-4-hydroxypyrrolidine-2-carboxylic acid, (2R,4R)—N-(iodoaceyl)-4-hydroxypyrrolidine-2-carboxylic acid, (2S,4R)—N-(iodoacetyl)-4-hydroxypyrrolidine-2-carboxylic acid, (2R,4S)—N-(iodoacetyl)-4-hydroxypyrrolidine-2-carboxylic acid, racemic N-(iodoacetyl)-cis-4-hydroxypyrrolidine-2-carboxylic acid, racemic N-(iodoacetyl)-trans-4-hydroxypyrrolidine-2-carboxylic acid, trimethylsilyl (2S,4S)—N-(iodoacetyl)-4-(trimethylsilyloxy)pyrrolidine-2-carboxylate, trimethylsilyl (2R,4R)—N-(iodoaceyl)-4-(trimethylsilyloxy)pyrrolidine-2-carboxylate, trimethylsilyl (2S,4R)—N-(iodoacetyl)-4-(trimethylsilyloxy)pyrrolidine-2-carboxylate, (2R,4S)—N-(iodoacetyl)-4-(trimethylsilyloxy)pyrrolidine-2-carboxylate, racemic trimethylsilyl N-(iodoacetyl)-cis-4-(trimethylsilyloxy)pyrrolidine-2-carboxylate, racemic trimethylsilyl N-(iodoacetyl)-trans-4-(trimethylsilyloxy)pyrrolidine-2-carboxylate, and other like compounds.

More preferable examples of formula (II') of the present invention include: (2S,4S)—N-(chloroacetyl)-4-hydroxypyrrolidine-2-carboxylic acid, (2S,4R)—N-(chloroacetyl)-4-hydroxypyrrolidine-2-carboxylic acid, trimethylsilyl (2S,4S)—N-(chloroacetyl)-4-(trimethylsilyloxy)pyrrolidine-2-carboxylate, trimethylsilyl (2S,4R)—N-(chloroacetyl)-4-(trimethylsilyloxy)pyrrolidine-2-carboxylate, (2S,4S)—N-(bromoacetyl)-4-hydroxypyrrolidine-2-carboxylic acid, (2S,4R)—N-(bromoacetyl)-4-hydroxypyrrolidine-2-carboxylic acid, trimethylsilyl (2S,4S)—N-(bromoacetyl)-4-(trimethylsilyloxy)pyrrolidine-2-carboxylate, trimethylsilyl (2S,4R)—N-(bromoacetyl)-4-(trimethylsilyoxy)pyrrolidine-2-carboxylate, (2S,4S)—N-(iodoacetyl)-4-hydroxypyrrolidine-2-carboxylic acid, (2S,4R)—N-(iodoacetyl)-4-hydroxypyrrolidine-2-carboxylic acid, trimethylsilyl (2S,4S)—N-(iodoacetyl)-4-(trimethylsilyloxy)pyrrolidine-2-carboxylate, and trimethylsilyl (2S,4R)—N-(iodoacetyl)-4-(trimethylsilyloxy)pyrrolidine-2-carboxylate.

Furthermore preferable examples of formula (II') of the present invention include: (2S,4R)—N-(chloroacetyl)-4-hydroxypyrrolidine-2-carboxylic acid, trimethylsilyl (2S,4R)—N-(chloroacetyl)-4-(trimethylsilyloxy)pyrrolidine-2-carboxylate, (2S,4R)—N-(bromoacetyl)-4-hydroxypyrrolidine-2-carboxylic acid, and trimethylsilyl (2S,4R)—N-(bromoacetyl)-4-(trimethylsilyloxy)pyrrolidine-2-carboxylate.

4-Fluoropyrrolidine-2-carbonyl fluoride compounds (formula (I)) of the present invention are useful intermediates for the preparation of various kinds of useful fluorinated compounds (see Examples 14~23). In particular, as exemplified in Scheme 5,4-fluoropyrrolidine-2-carbonyl fluoride compounds of the present invention are useful compounds which significantly reduce the number of necessary reaction steps for the preparation of useful fluoro intermediates such as compounds F, G, H, I, J, K, and L, which have been prepared via many reaction steps by the conventional methods as discussed above (shown in the Background of the Invention section). For example, a (2S,4S)-4-fluoropyrrolidine-2-carbonyl fluoride is reacted with ammonia to give useful (2S,4S)-4-fluoropyrrolidine-2-carboxamide (F) (see Examples 14 and 15). N-deprotection of compound (F) produces (2S,4S)-4-fluoropyrrolidine-2-carboxamide or its salt (G) (see Example 22). Compound (F) is dehydrated to give the useful N-substituted (2S,4S)-4-fluoropyrrolidinie-2-carbonitrile (I) (see Example 20), N-deprotection of which produces (2S,4S)-4-fluoropyrrolidine-2-carbonitrile or its salt (J) (see Example 23). (2S,4S)—N-haloacetyl-4-fluoropyrrolidine-2-carbonyl fluoride is reacted with ammonia to give useful (2S,4S)—N-haloacetyl-4-fluoropyrrolidine-2-carboxamide (K) (see Example 19), dehydration of which produces (2S,4S)—N-haloacetyl-4-fluoropyrrolidine-2-carbonitrile (L) (see Example 21). Reaction of (2S,4S)-4-fluoropyrrolidine-2-carbonyl fluoride with O,N-dimethylhydroxylamine produces useful N-substituted (2S,4S)-4-fluoropyrrolidine-2-(N-methoxy-N-methylcarboxamide) (H) (see Example 18). Useful N-substituted (2S,4S)-4-fluoropyrrolidine-2-carboxylate methyl esters (D) are also given in high yield from the compounds (formula (I)) of the present invention (see Examples 16 and 17).

Scheme 5

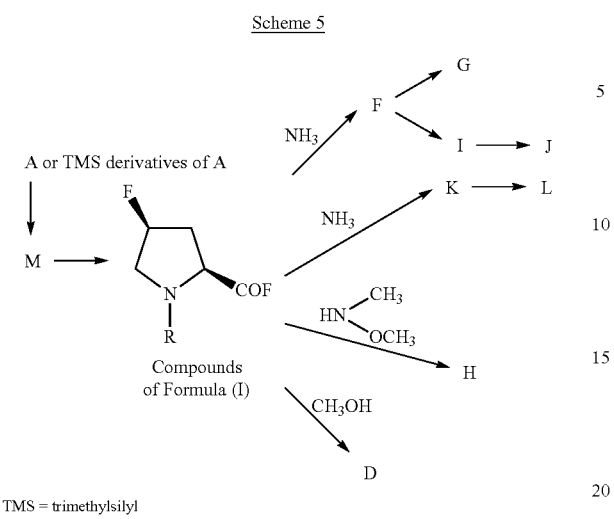

TMS = trimethylsilyl

The present invention provides 4-fluoropyrrolidine-2-carbonyl fluoride compounds having the formula (I) and useful preparative methods for them. As shown in Examples below, the 4-fluoropyrrolidine-2-carbonyl fluoride compounds (formula (I)) are useful fluoro intermediate compounds for the preparation of medicines such as inhibitors and other like therapeutics.

The following examples will illustrate the present invention in more details, but it should be understood that the present invention is not deemed to be limited thereto.

EXAMPLES

The following examples are provides for illustrative purposes only and are not intended to limit the scope of the invention. Tables 1 and 2 provide formula numbers, names, and structures for reference when reviewing the following examples.

TABLE 1

4-Fluoropyrrolidine-2-carbonyl fluoride compounds (Formulas Ia-If):

| Formula Number | Name | Structure |
|---|---|---|
| Ia | (2S,4S)-N-Fmoc-4-fluoropyrrolidine-2-carbonyl fluoride | 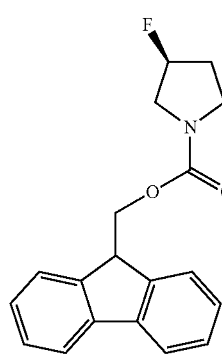 |
| Ib | (2S,4R)-N-Fmoc-4-fluoropyrrolidine-2-carbonyl fluoride | 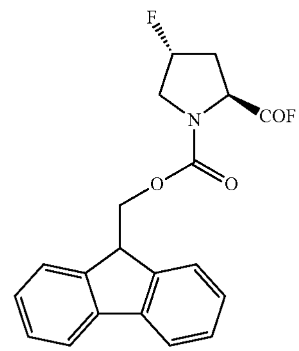 |
| Ic | (2S,4S)-N-Cbz-4-fluoropyrrolidine-2-carbonyl fluoride | 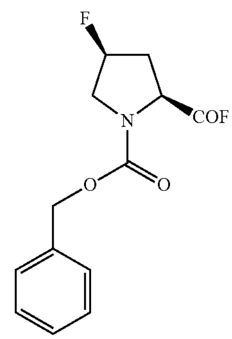 |
| Id | (2S,4S)-N-Boc-4-fluoropyrrolidine-2-carbonyl fluoride | 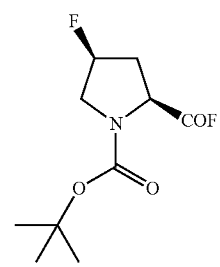 |
| Ie | (2S,4R)-N-Boc-4-fluoropyrrolidine-2-carbonyl fluoride | 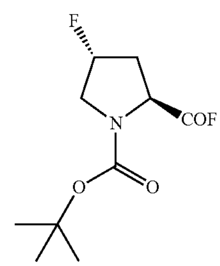 |
| If | (2S,4S)-N-chloroacetyl-4-fluoropyrrolidine-2-carbonyl fluoride | 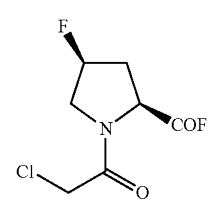 |

Fmoc = 9-fluorenylmethoxycarbonyl.
Cbz = benzyloxycarbonyl.
Boc = tert-butoxycarbonyl.

TABLE 2

Useful compounds derived from 4-fluoropyrrolidine-2-carbonyl fluoride compounds of formula (I) of the present invention

| Formula Number | Name | Structure |
|---|---|---|
| Da | Methyl (2S,4S)-N-Fmoc-4-fluoro-pyrrolidine-2-carboxylate | 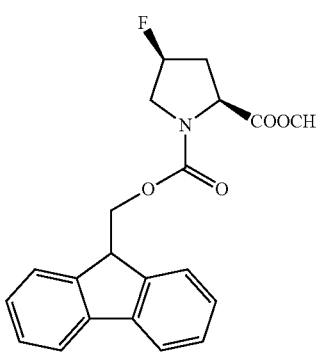 |
| Db | Methyl (2S,4S)-N-Cbz-4-fluoro-pyrrolidine-2-carbxylate | 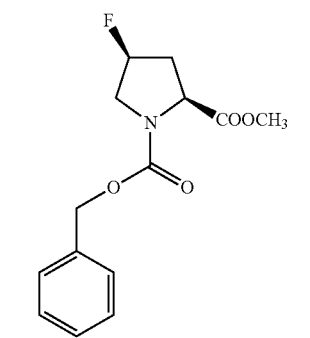 |
| Fa | (2S,4S)-N-Fmoc-4-fluoro-pyrrolidine2-carboxamide | 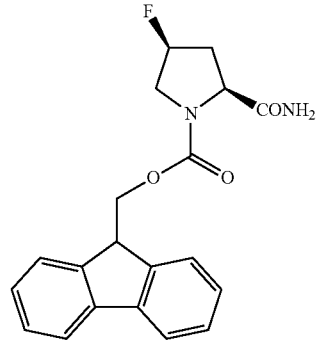 |
| Fb | (2S,4S)-N-Cbz-4-fluoro-pyrrolidine-2-carboxamide | 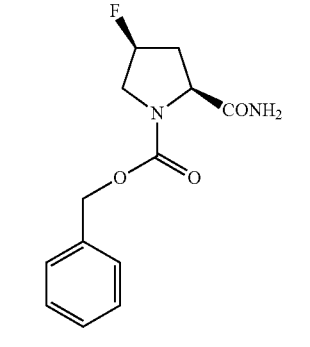 |
| Ga | (2S,4S)-4-fluoro-pyrrolidine-2-carboxamide hydrochloride | 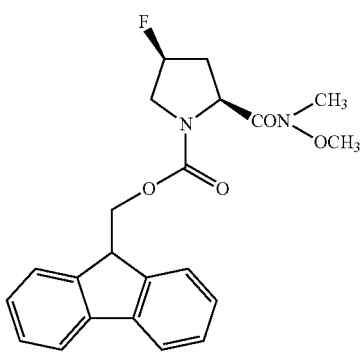 |
| Ha | (2S,4S)-N-Fmoc-4-fluoro-pyrrolidine-2-(N-methyl-N-methoxy-carboxamide) | 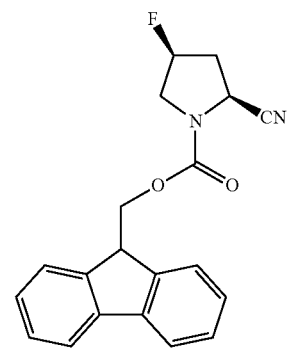 |
| Ia | (2S,4S)-N-Fmoc-4-fluoro-pyrrolidine-2-carbonitrile | |

TABLE 2-continued

Useful compounds derived from 4-fluoropyrrolidine-2-carbonyl fluoride compounds of formula (I) of the present invention

| Formula Number | Name | Structure |
|---|---|---|
| Ja | (2S,4S)-4-fluoro-pyrrolidine-2-carbonitrile hydrochloride | 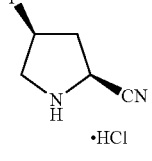 |
| Ka | (2S,4S)-N-chloroacetyl-4-fluoro-pyrrolidine-2-carboxamide | 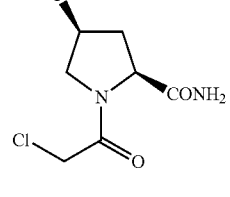 |
| La | (2S,4S)-N-chloroacetyl-4-fluoro-pyrrolidine-2-carbonitrile | 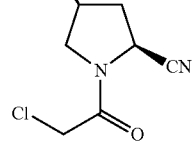 |

Fmoc = 9-fluorenylmethoxycarbonyl.
Cbz = benzyloxycarbonyl.

Example 1

Preparation of (2S,4S)—N-Fmoc-4-fluoropyrrolidine-2-carbonyl fluoride (Ia)

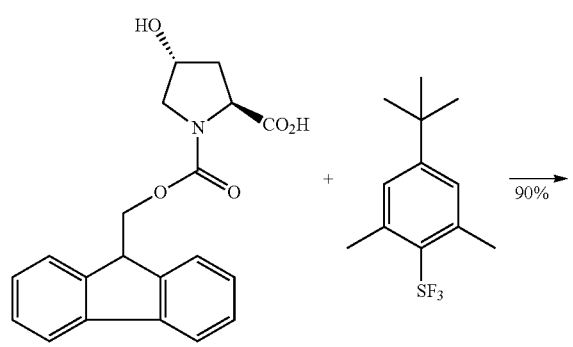

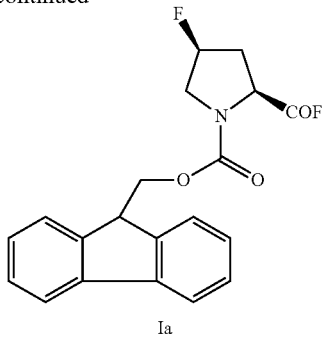

Ia

N-Fmoc-trans-4-hydroxy-L-proline (from Sigma-Aldrich) (5.10 g, 14.4 mmol) was placed in a fluoropolymer (PFA) vessel and suspended in 20 ml of dry dichloromethane. It was cooled to about 0° C. on an ice bath. A solution of 4-tert-butyl-2,6-dimethylphenylsulfur trifluoride (9.03 g, 36.1 mmol) in 10 ml of dry dichloromethane was added slowly for 20 min. After complete addition, it was stirred for 0.5 h, and then the ice bath was removed. Stirring was continued at room temperature for 60 h. Analysis of the reaction mixture with NMR showed that the yield of product was 90%. The solvent was removed at reduced pressure, and then, to the resulting residue, diethyl ether (20 ml) added followed by the addition of pentane (20 ml). Stirring the mixture well gave a solid, which was then washed with pentane (25 ml×2). The solid was dissolved in dichloromethane and precipitated out by adding pentane to the solution, giving 3.86 g (78%) of pure (2S,4S)—N-Fmoc-4-fluoropyrrolidine-2-carbonyl fluoride (Ia) as white powder: mp 127-128° C.: $^{19}$F-NMR (CDCl$_3$) δ (as a 56:44 mixture of two rotamers) 28.34 (s, 0.56 F, COF) and 28.16 (s, 0.44 F, COF), −172.80 (m, 1 F, CHF): $^1$H-NMR (CDCl$_3$) δ (as a mixture of two rotamers) 2.25-2.7 (m, 2H), 3.50-4.0 (m, 2H), 4.20-4.85 (m, 4H), 5.10-5.45 (m, 1H), 7.25-7.85 (m, 8H): $^{13}$C-NMR (CDCl$_3$) (as a mixture of two rotamers) δ 90.71 (d, J=177.7 Hz, CF), 91.78 (d, J=177.7 Hz, CF), 153.81 (s, CON), 154.44 (s, CON), 160.99 (d, J=371.3 Hz, COF): High Resolution Mass/ESI-APCI method (solvent; methanol); (M+Na)$^+$ 380.1070 [calcd 380.1069 for (C$_{20}$H$_{17}$F$_2$NO$_3$+Na)].

Examples 2~10

Preparation of 4-fluoropyrrolidine-2-carbonyl fluoride Compounds (Ia), (Ib), (Ic), (Id), and (If)

4-Fluoropyrrolidine-2-carbonyl fluoride compounds (Ia), (Ib), (Ic), (Id), and (If) were prepared by reaction of the corresponding 4-hydroxypyrrolidine-2-carboxylic acid compound with a fluorinating agent in the same manner as described in Example 1. The results and reaction conditions are shown in Table 3 together with those of Example 1.

TABLE 3

Preparation of 4-fluoropyrrolidine-2-carbonyl fluoride compounds from 4-hydroxypyrrolidine-2-carboxylic acid compounds with various fluorinating agents

| Ex | (II) | Fluorinating agent | Solvent | Conditions and Additives | Product (I) | Yield* |
|---|---|---|---|---|---|---|
| 1 | 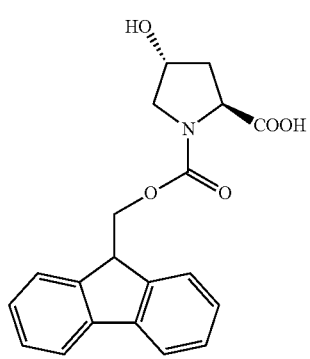<br>14.4 mmol | 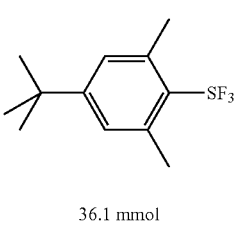<br>36.1 mmol | $CH_2Cl_2$<br>30 mL | ~0° C. → r.t.<br>1 h, and then<br>r.t., 60 h | 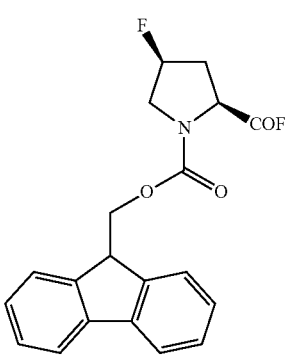<br>(Ia) | 90%<br>(78%) |
| 2 | 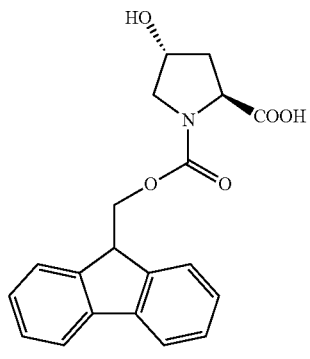<br>1.46 mmol | 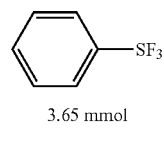<br>3.65 mmol | $CH_2Cl_2$<br>5 mL | ~0° C. → r.t.<br>1 h, and then<br>r.t., 60 h | 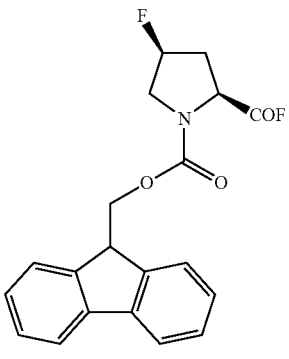<br>(Ia) | 68% |
| 3 | 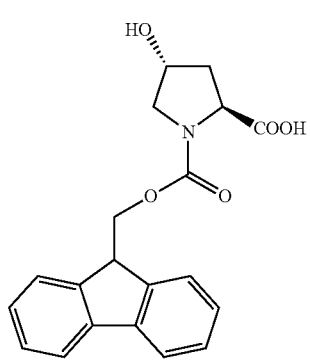<br>1.29 mmol | 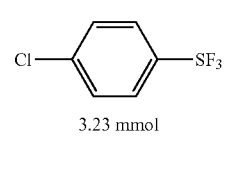<br>3.23 mmol | $CH_2Cl_2$<br>5 mL | ~0° C. → r.t.<br>1 h, and then<br>r.t., 60 h | 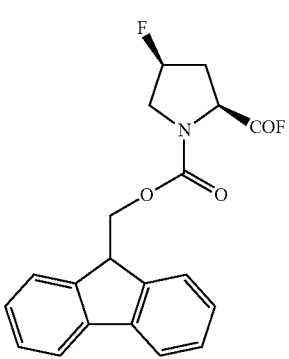<br>(Ia) | 54% |

TABLE 3-continued

Preparation of 4-fluoropyrrolidine-2-carbonyl fluoride compounds from 4-hydroxypyrrolidine-2-carboxylic acid compounds with various fluorinating agents

| Ex | (II) | Fluorinating agent | Solvent | Conditions and Additives | Product (I) | Yield* |
|---|---|---|---|---|---|---|
| 4 | 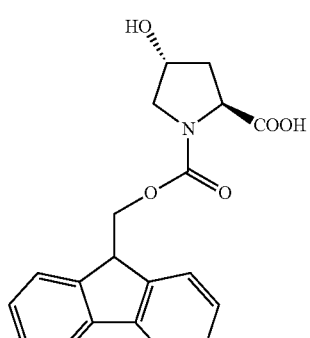<br>1.5 mmol | 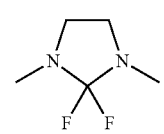<br>3.75 mmol | CH$_2$Cl$_2$<br>5 mL | ~0° C. → r.t.<br>1 h, and then<br>r.t., 60 h | 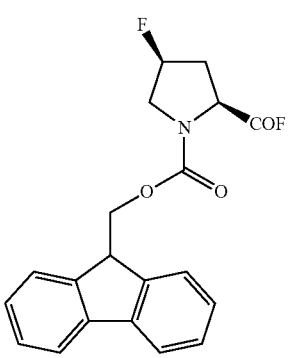<br>(Ia) | 68%<br>(50%) |
| 5 | 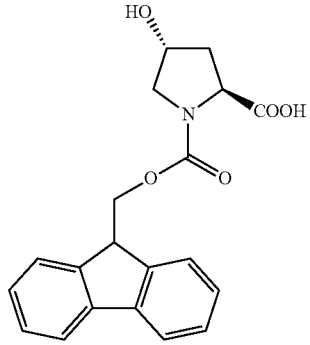<br>1.47 mmol | (C$_2$H$_5$)$_2$NSF$_3$<br>3.67 mmol | CH$_2$Cl$_2$<br>5 mL | ~0° C. → r.t.<br>1 h, and then<br>r.t., 60 h | 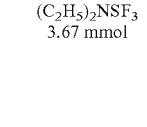<br>(Ia) | 40% |
| 6 | 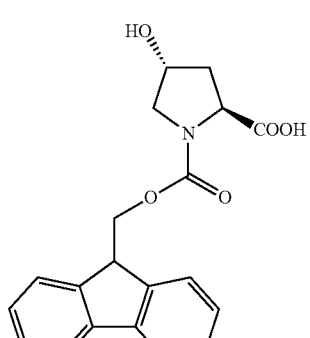<br>1.47 mmol | 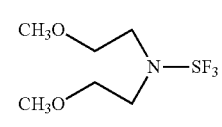<br>3.67 mmol | CH$_2$Cl$_2$<br>5 mL | ~0° C. → r.t.<br>1 h, and then<br>r.t., 60 h | 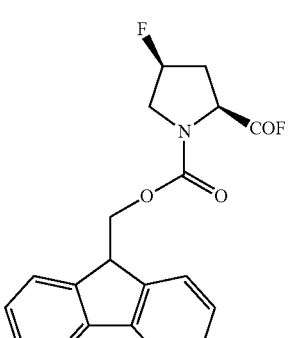<br>(Ia) | 45% |

TABLE 3-continued

Preparation of 4-fluoropyrrolidine-2-carbonyl fluoride compounds from 4-hydroxypyrrolidine-2-carboxylic acid compounds with various fluorinating agents

| Ex | (II) | Fluorinating agent | Solvent | Conditions and Additives | Product (I) | Yield* |
|---|---|---|---|---|---|---|
| 7 | 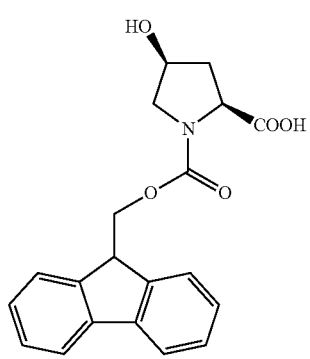<br>2.26 mmol | 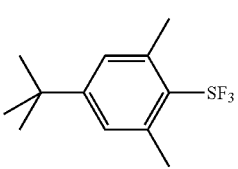<br>5.66 mmol | CH₂Cl₂ 5 mL | ~0° C., 1 h, and then r.t., 60 h | 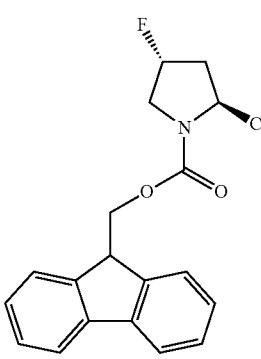<br>(Ib) | 36% |
| 8 | 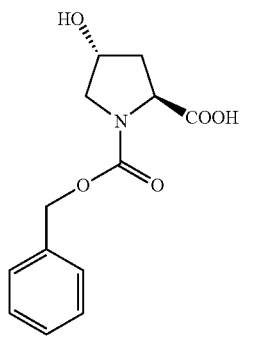<br>10 mmol | 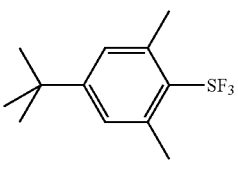<br>25 mmol | CH₂Cl₂ 30 mL | ~0° C. → r.t. 1 h, and then r.t., 60 h | 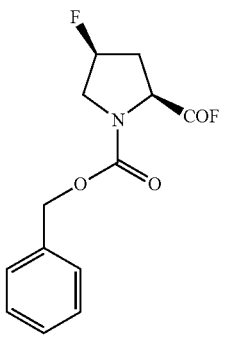<br>(Ic) | 90% (75%) |
| 9 | 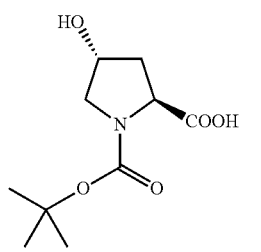<br>1.5 mmol | 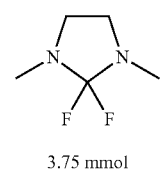<br>3.75 mmol | CH₂Cl₂ 5 mL | ~0° C. → r.t. 1 h, and then r.t., 60 h | 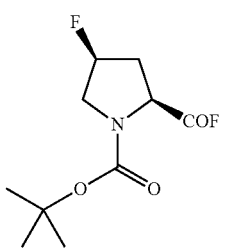<br>(Id) | (50%) |
| 10 | 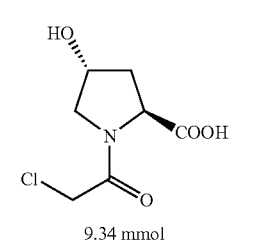<br>9.34 mmol | 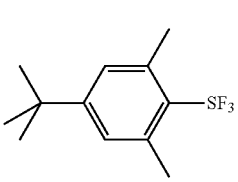<br>23.3 mmol | CH₂Cl₂ 25 mL | ~0° C. → r.t. 1 h, and then r.t., 72 h | 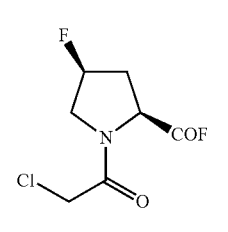<br>(If) | 90% (76%) |

*Yields are determined based on ¹⁹F NMR, and yields given in parentheses are isolated yields.

The properties and spectral data of the 4-fluoropyrrolidine-4-carbonyl fluoride compounds (Ia)~(Id), (If) are shown in the following:

(2S,4S)—N-Fmoc-4-fluoropyrrolidine-2-carbonyl fluoride (Ia): see Example 1.

(2S,4R)—N-Fmoc-4-fluoropyrrolidine-2-carbonyl fluoride (Ib): see Example 11.

(2S,4S)—N-Cbz-4-fluoropyrrolidine-2-carbonyl fluoride (Ic): Oil: $^{19}$F-NMR (CDCl$_3$) δ (as a 53:47 mixture of two rotamers) 28.50 (s, 0.47 F, COF), 28.38 (s, 0.53 F, COF), −173.0 (m, 1 F): $^1$H-NMR (CDCl$_3$) δ 2.20-2.70 (m, 2H), 3.5-4.1 (m, 2H), 4.65-4.8 (m, 1H), 5.0-5.5 (m, 3H), 7.3-7.50 (m, 5H): $^{13}$C-NMR (CDCl$_3$) δ (as a mixture of two rotamers) δ1.07 (d, J=177.0 Hz, CF), 92.06 (d, J=177.0 Hz, CF), 153.92 (s, CON), 154.60 (s, CON), 161.42 (d, J=371 Hz, COF), 161.57 (d, J=371.3 Hz, COF): High Resolution Mass/ESI-APCI method (solvent; methanol); (M-F+OCH$_3$+Na)$^+$ 304.0959 [calcd 304.0956 for (C$_{14}$H$_{16}$FNO$_4$+Na)].

(2S,4S)—N-Boc-4-fluoropyrrolidine-2-carbonyl fluoride (Id): see Example 12.

(2S,4S)—N-chloroacetyl-4-fluoropyrrolidine-2-carbonyl fluoride (If): Oil: $^{19}$F-NMR (CDCl$_3$) δ 28.58 (s, 1 F, COF), −173.36 (m, 1 F, CHF): $^1$H-NMR (CDCl$_3$) δ 2.2-2.8 (m, 2H), 3.7-4.2 (m, 4H), 4.6-5.0 (m, 1H), 5.1-5.5 (m, 1H): $^{13}$C-NMR (CDCl$_3$) δ 34.87 (d, J=21.6 Hz), 41.64, 53.26 (d, J=23.8 Hz), 56.13 (d, J=66.5 Hz), 58.21, 91.26 (d, J=178.4 Hz, CF), 160.50 (d, J=369.9 Hz, COF), 165.90 (s, CO): High Resolution Mass/ESI-APCI method (solvent; methanol); (M-F+OCH$_3$+Na)$^+$ 246.0308 [calcd 246.0304 for (C$_8$H$_{11}$ClFNO$_3$+Na)].

Example 11

Preparation of (2S,4R)—N-Fmoc-4-fluoropyrrolidine-2-carbonyl fluoride (Ib)

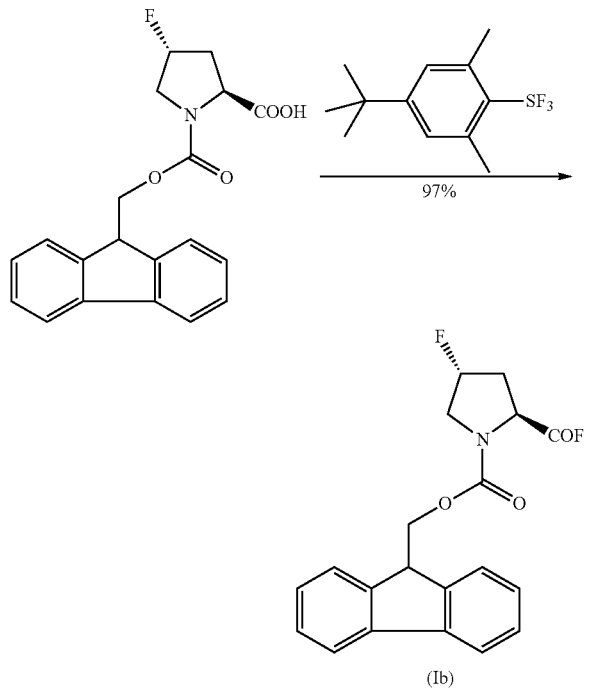

A solution of 4-(tert-butyl)-2,6-dimethylphenylsulfur trifluoride (10.5 mmol) in 5 ml of dichloromethane was added slowly to a stirred solution of (2S,4R)—N-Fmoc-4-fluoropyrrolidine-2-carboxylic acid (7 mmol) in 15 mL of dichloromethane in a fluoropolymer (PFA) reactor cooled on an ice bath. After complete addition, the ice bath was removed and stirred at room temperature for 0.5 h. $^{19}$F NMR analysis of the reaction mixture showed that (2S,4R)—N-Fmoc-4-fluoropyrrolidine-2-carbonyl fluoride (Ib) was produced in 97% yield. All the volatiles were removed at reduced pressure, and dichloromethane (2 ml) was added to the residue, followed by the addition of pentane (30 ml). After stirring well, a supernatant liquid was removed and the residue was washed with pentane (25 ml×2). Finally the product (Ib) (1.75 g, 70% yield) was obtained as white powder by dissolving the solid in dichloromethane and precipitating with pentane. $^{19}$F-NMR (CDCl$_3$) (a 6:4 mixture of two rotamers) δ 29.69 (s, 0.6 F, COF), 29.39 (s, 0.6 F, COF), −177.05 (m, 0.6 F, CF), −177.99 (m, 0.4 F, CF): $^1$H-NMR (CDCl$_3$) δ (as a mixture of rotamers) 2.0-2.9 (m, 2H), 3.4-4.8 (m, 6H), 5.05-5.5 (m, 1H), 7.2-7.9 (m, 8H): $^{13}$C-NMR (CDCl$_3$) δ (as a mixture of two rotamers) δ0.40 (d, J=179.9 Hz, CF), 91.39 (d, J=180.6 Hz, CF), 154.16 (CON), 154.85 (CON), 161.49 (d, J=367.8 Hz, COF): High Resolution Mass/ESI-APCI method (solvent; methanol); (M-F+OCH$_3$+Na)$^+$392.1272 [calcd 392.1269 for (C$_{21}$H$_{20}$FNO$_4$+Na)].

Example 12

Preparation of (2S,4S)—N-Boc-4-fluoropyrrolidine-2-carbonyl fluoride (Id)

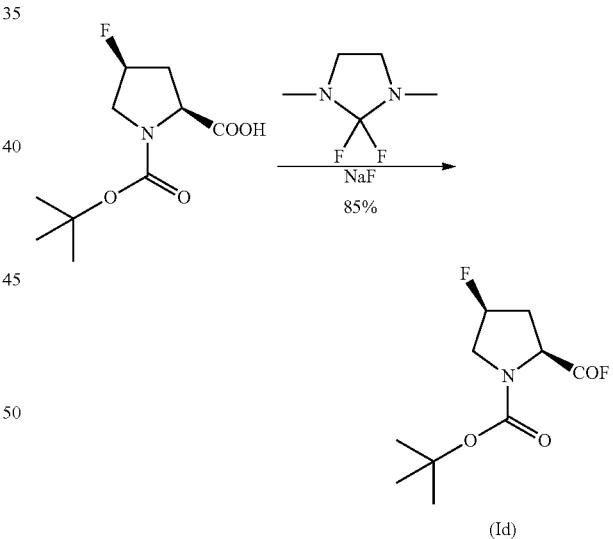

(2S,4S)—N-Boc-4-fluoropyrrolidine-2-carboxylic acid (1.17 g, 5 mmol) and sodium fluoride (0.63 g, 15 mmol) were put in a fluoropolymer (PFA) vessel, and 10 ml of dichloromethane was added into the vessel. The mixture was cooled with ice. A solution of 2,2-difluoro-1,3-dimethylimidazolidine (817 mg, 6 mmol) in 2 ml of dichloromethane was added slowly. After 5 minutes of addition, the ice bath was removed and the mixture warmed to room temperature. The reaction mixture was stirred for a total 20 min. $^{19}$F NMR analysis of the reaction mixture showed that (2S,4S)—N-Boc-4-fluoropyrrolidine-2-carbonyl fluoride (Id) was produced in 85% yield. The mixture was diluted with 10 ml of dichloromethane and washed with water. The organic layer was dried over anhydrous magnesium sulfate and filtered. Removal of solvent followed by washing with a small amount of water and then drying gave 846 mg (yield 72%) of (2S,4S)—N-Boc-4-fluoropyrrolidine-2-carbonyl fluoride (Id): Oil: $^{19}$F-NMR (CDCl$_3$) (as a 6:4 mixture of two rotamers) δ 28.22 (s, 0.6 F, COF), 28.14 (s, 0.4 F, COF), −173.18 (m, 1 F, CF): $^1$H-NMR (CDCl$_3$) δ (as a mixture of two rotamers) 1.40 (s, 0.55×9H, t-Bu), 1.43 (s, 0.45×9H, t-Bu), 2.2-2.6 (m, 2H), 3.45-3.95 (m, 2H), 4.5-4.7 (m, 1H), 5.22 (br.d, J=51.9 Hz, 1H, CHF): $^{13}$C-NMR (CDCl$_3$) δ (as a mixture of two rotamers); 90.94 (d, J=177.0 Hz, 1H, CF), 92.02 (d, J=177.0 Hz, CF), 153.06 (s, CON), 153.82 (s, CON), 161.50 (d, J=372.1 Hz, COF), 161.66 (d, J=372.8 Hz, COF): High Resolution Mass/ESI-APCI method (solvent; methanol); (M-F+OCH$_3$+Na)$^+$ 270.1109 [calcd 270.1112 for (C$_{11}$H$_{18}$FNO$_4$+Na)].

Example 13

Preparation of (2S,4R)—N-Boc-4-fluoropyrrolidine-2-carbonyl fluoride (Ie)

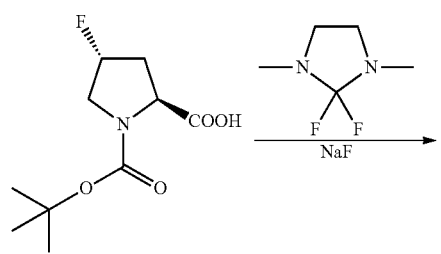

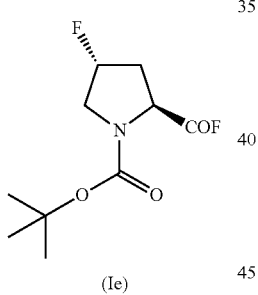

(2S,4R)—N-Boc-4-fluoropyrrolidine-2-carboxylic acid (1.17 g, 5.0 mmol) and NaF (0.63 g, 15 mmol) were taken in a Teflon® reactor and suspended in 10 ml of anhydrous dichloromethane. It was cooled with ice. A solution of 2,2-difluoro-1,3-dimethylimidazolidine (0.817 g, 6.0 mmol) in 2 ml of dichloromethane was slowly added. After 5 minutes stirring, the ice bath was removed and stirring was continued at room temperature for 20 minutes. All the volatiles were removed at reduced pressure and the obtained viscous liquid was mixed with 50 ml of pentane and washed with water (50 ml×2). The organic layer was dried over anhydrous magnesium sulfate and filtered. Removal of solvent at reduced pressure gave 1.06 g of (2S,4R)—N-Boc-4-fluoropyrrolidine-2-carbonyl fluoride (Ie) as a colorless oil. Yield; 90%. $^{19}$F NMR (282 MHz, CDCl$_3$) (as a 4:6 mixture of rotamers) δ (ppm) 28.66 (s, 0.4 F, COF), 28.10 (s, 0.6 F, COF), −177.16 (m, 0.4 F, CF), −177.83 (m, 0.6 F, CF): $^1$H NMR (300 MHz, CDCl$_3$) (as a mixture of rotamers) δ 1.42 (s, 0.6×9H, t-Bu), 1.44 (s, 0.4×9H, t-Bu), 2.0-2.8 (m, 2H), 3.45-4.0 (m, 2H), 4.51 (m, 1H), 5.22 (dm, 1H, J=51.6 Hz): $^{13}$C NMR (75 MHz, CDCl$_3$) (as a mixture of two rotamers) δ 90.70 (d, J=179.9 Hz, CF), 91.61 (d, J=179.9 Hz, CF), 153.07 (s, CON), 154.17 (s, CON), 161.90 (d, J=368.4 Hz, COF), 162.11 (d, J=368.4 Hz, COF): IR (Neat, KBr) 1848 (COF) cm$^{-1}$: High Resolution Mass/ESI-APCI method (solvent; methanol); (M-F+OCH$_3$+Na)$^+$ 270.1114 [calcd 270.1112 for (C$_{11}$H$_{18}$FNO$_4$+Na)].

Example 14

Reaction of (2S,4S)—N-Fmoc-4-fluoropyrrolidine-2-carbonyl fluoride (Ia) with ammonia; Preparation of (2S,4S)—N-Fmoc-4-fluoropyrrolidine-2-carboxamide (Fa)

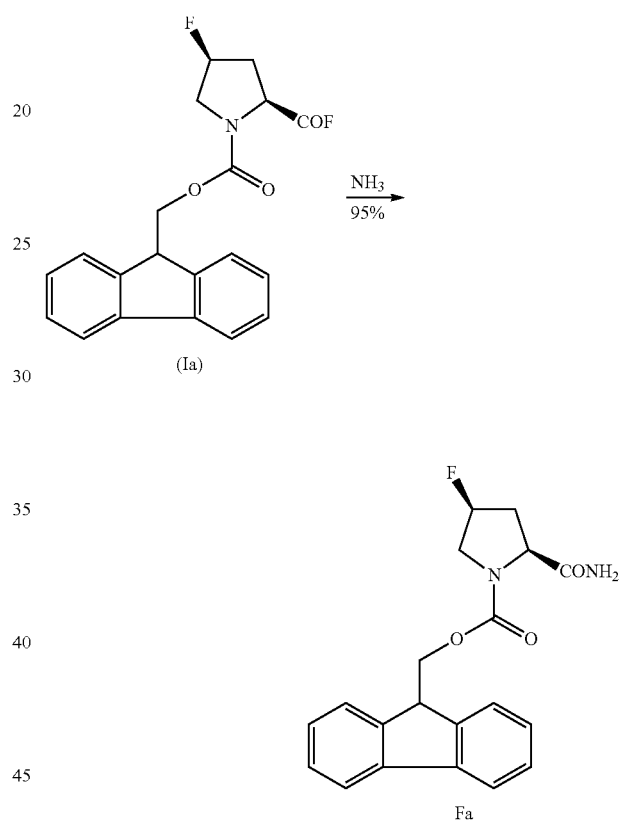

(2S,4S)—N-Fmoc-4-fluoropyrrolidine-2-carbonyl fluoride (Ia) (355 mg, 1 mmol), prepared according to Example 1, was dissolved in 5 ml of dichloromethane. Into the solution, an aqueous 28-30% ammonia solution (NH$_3$, 2.2 mmol) was added drop wise at room temperature. The reaction mixture was stirred at room temperature for 0.5 h. The reaction mixture was extracted with dichloromethane and the organic layer was washed with water, dried over MgSO$_4$, and filtered. Removal of solvent at reduced pressure gave a solid, which was crystallized from dichloromethane and pentane (1:3) to give (2S,4S)—N-Fmoc-4-fluoropyrrolidine-2-carboxamide (Fa) as white crystals. Yield: 335 mg (95%). $^{19}$F-NMR (CDCl$_3$) δ (as a 52:48 mixture of two rotamers)-174.56 (m, 0.52 F), −173.02 (m, 0.48 F): $^1$H-NMR (CDCl$_3$) δ 1.90-2.90 (m, 2H), 3.2-3.95 (m, 2H), 4.0-4.8 (m, 4H), 5.15 (d, 1H, J=52 Hz), 5.8-6.5 (m, 2H), 7.1-8.0 (m, 8H): $^{13}$C-NMR (CDCl$_3$) δ (as a mixture of two rotamers) 91.59 (d, J=175.5 Hz, CF), 92.18 (d, J=177.0 Hz, CF), 155.33 (s, CON), 155.77 (s, CON), 173.75 (s, CONH$_2$), 174.25 (s, CONH$_2$).

Example 15

Reaction of (2S,4S)—N-Cbz-4-fluoropyrrolidine-2-carbonyl fluoride (Ic) with ammonia; Preparation of (2S,4S)—N-Cbz-4-fluoropyrrolidine-2-carboxamide (Fb)

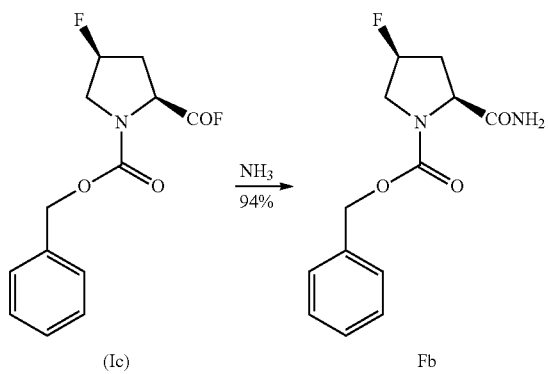

(2S,4S)—N-Cbz-4-fluoropyrrolidine-2-carbonyl fluoride (Ic) (807 mg, 2 mmol), which was prepared according to Example 7 was dissolved in 5 ml of dichloromethane. Into the solution, an aqueous 28-30% ammonia solution (NH$_3$, 6.6 mmol) was added drop wise at room temperature. The mixture was stirred at room temperature for 0.5 h. The reaction mixture was extracted with dichloromethane, and the organic layer was washed with water, dried over MgSO$_4$ and filtered. Removal of solvent at reduced pressure gave a solid, which was crystallized from dichloromethane and pentane (1:3) to give (2S,4S)—N-Fmoc-4-fluoropyrrolidine-2-carboxamide (Fb) as white crystals. Yield: 751 g (94%). $^{19}$F-NMR (CDCl$_3$) δ (as a 1:1 mixture of two rotamers)-172.8 (m, 0.5 F), −174.2 (m, 0.5 F): $^1$H-NMR (CDCl$_3$) δ 2.0-2.70 (m, 2H), 3.4-4.0 (m, 2H), 4.43 (m, 1H), 5.0-5.5 (m, 3H), 6.1-6.8 (m, 2H), 7.1-7.7 (m, 5H); $^{13}$C-NMR (CDCl$_3$) δ (as a mixture of two rotamers) δ1.69 (d, J=176.3 Hz, CF), 92.30 (d, J=178.4 Hz, CF), 155.25 (CON), 155.83 (CON), 174.06 (CONH$_2$), 174.73 (CONH$_2$).

Example 16

Reaction of (2S,4S)—N-Fmoc-4-fluoropyrrolidine-2-carbonyl fluoride (Ia) with methanol; Preparation of methyl (2S,4S)—N-Fmoc-4-fluoropyrrolidine-2-carboxylate (Da)

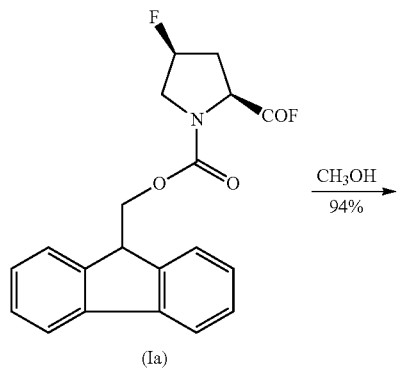

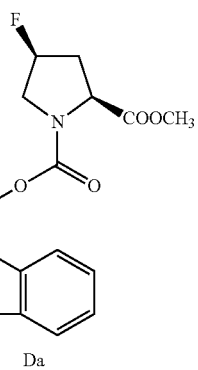

(2S,4S)—N-Fmoc-4-fluoropyrrolidine-2-carbonyl fluoride (Ia) (1 mmol) was dissolved in 5 ml of dichloromethane. Into the reaction, an excess of methanol was added at room temperature. The reaction mixture was stirred at room temperature for 1 h. The mixture was extracted with dichloromethane, and the organic layer was washed with water, dried over MgSO$_4$ and filtered. Removal of solvent at reduced pressure gave a solid, which was crystallized from dichloromethane and pentane (1:3) to give methyl (2S,4S)—N-Fmoc-4-fluoropyrrolidine-2-carboxylate (Da) as white crystals. Yield: 345 mg (94%). $^{19}$F-NMR δ (CDCl$_3$)-172.7 (m, 1 F): $^1$H-NMR (CDCl$_3$) (as an about 53:47 mixture of two rotamers) δ 2.2-2.7 (m, 2H), 3.6-4.0 (m, 5H; including two CH$_3$ singlets at 3.67 as a minor rotamer and 3.76 as a major rotamer), 4.15-4.7 (m, 4H), 5.20 (dm, J=52.6 Hz, 0.47H), 5.25 (dm, J=52.3 Hz, 0.53H), 7.2-87.9 (m, 8H); $^{13}$C-NMR (CDCl$_3$) (as a mixture of two rotamers) δ 92.18 (d, J=177.7 Hz, CF), 91.17 (d, J=177.0 Hz, CF), 154.40 (s, CON), 154.63 (s, CON), 171.63 (s, COO), 171.79 (s, COO).

Example 17

Reaction of (2S,4S)—N-Cbz-4-fluoropyrrolidine-2-carbonyl fluoride (Ic) with methanol; Preparation of methyl (2S,4S)—N-Cbz-4-fluoropyrrolidine-2-carboxylate (Fa)

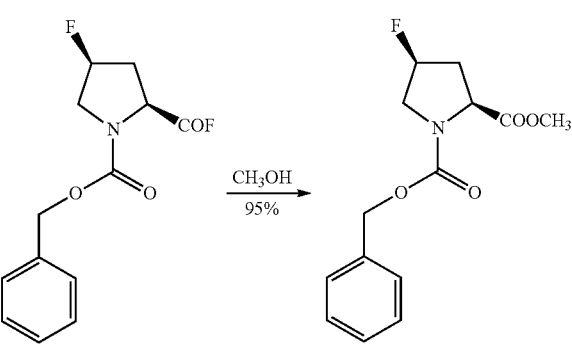

(2S,4S)—N-Cbz-4-fluoropyrrolidine-2-carbonyl fluoride (Ic) (1 mmol) was dissolved in 5 ml of dichloromethane. Into the solution, methanol (excess) was added at room temperature, followed by the addition of triethylamine (1.5 mmol). The mixture was stirred at room temperature for 1 h. The reaction mixture was extracted with dichloromethane, and the organic layer was washed with water, dried over MgSO$_4$ and filtered. Removal of solvent at reduced pressure gave methyl (2S,4S)—N-Cbz-4-fluoropyrrolidine-2-carboxylate (Fa). Yield: 266 mg (95%). $^{19}$F-NMR (CDCl$_3$) δ −172.8 (m): $^1$H-NMR (CDCl$_3$) δ (as an about 53:47 mixture of two rotamers) 2.2-2.6 (m, 2H), 3.6-4.0 (m, 5H, including two CH$_3$ singlet peaks at 3.63 as a minor rotamer and 3.74 as a major rotamer), 4.53 (d, J=9.3 Hz, 0.47H), 4.60 (d, J=9.6 Hz, 0.53H), 5.0-5.4 (m, 3H), 7.2-7.5 (m, 5H): $^{13}$C-NMR (CDCl$_3$) (as a mixture of two rotamers) δ 92.24 (d, J=177.0 Hz, CF), 91.25 (d, J=177.0 Hz, CF), 154.23 (s, CON), 154.57 (s, CON), 171.64 (s, COO), 171.91 (s, COO).

Example 18

Reaction of (2S,4S)—N-Fmoc-4-fluoropyrrolidine-2-carbonyl fluoride (Ia) with N,O-dimethylhydroxylamine; Preparation of N-Fmoc-4-fluoropyrrolidine-2-(N-methyl-N-methoxycarboxamide) (Ha)

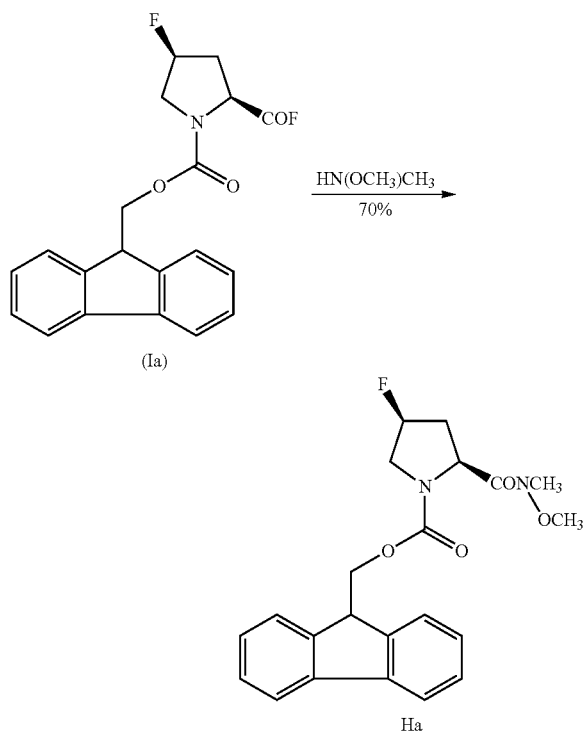

(2S,4S)—N-Fmoc-4-fluoropyrrolidine-2-carbonyl fluoride (Ia) (355 mg, 1 mmol) was dissolved in 5 ml of dichloromethane. Into the mixture was added a dichloromethane solution of N,O-dimethylhydroxylamine (in situ prepared from 1.5 mmol of N,O-dimethylhydroxylamine hydrochloride and 1.2 mmol of diisopropylethylamine in 2 mL of dichloromethane at 0° C.). The reaction mixture was stirred at room temperature for 6 h. The mixture was extracted with dichloromethane and the organic layer was washed with water, dried over MgSO$_4$ and filtered. Removal of solvent at reduced pressure gave a solid, which was crystallized from a 1:3 mixture of dichloromethane and pentane and gave N-Fmoc-4-fluoropyrrolidine-2-(N-methyl-N methoxycarboxamide) (Ha) as white crystals in 85% yield. Further purification by chromatography on silica gel gave a pure product, 279 mg (yield 70%). $^{19}$F-NMR (CDCl$_3$) δ −171.38 (m, 1 F): $^1$H-NMR (CDCl$_3$) δ (as a 6:4 mixture of two rotamers) 2.30-2.60 (m, 2H), 3.12 (s, 0.4×3H, NCH$_3$), 3.23 (s, 0.6×3H, NCH$_3$), 3.47 (s, 0.4×3H, OCH$_3$), 3.76 (s, 0.6×3H, OCH$_3$), 3.60-4.85 (m, 6H except a peak at 3.76), 5.18 (dm, J=53.3 Hz, 0.4H, CHF), 5.27 (dm, J=53.3 Hz, 0.6H, CHF), 7.2-7.9 (m, 8H): $^{13}$C-NMR (CDCl$_3$) δ (as a mixture of two rotamers) δ 1.75 (d, J=179.9 Hz, CF), 90.78 (d, J=179.2 Hz, CF), 154.38 (s, CON), 154.73 (s, CON), 171.13 (s, CONO), 171.29 (s, CONO).

Example 19

Reaction of (2S,4S)—N-(chloroacetyl)-4-fluoropyrrolidine-2-carbonyl fluoride (If) with ammonia; Preparation of (2S,4S)—N-chloroacetyl-4-fluoropyrrolidine-2-carboxamide (Ka)

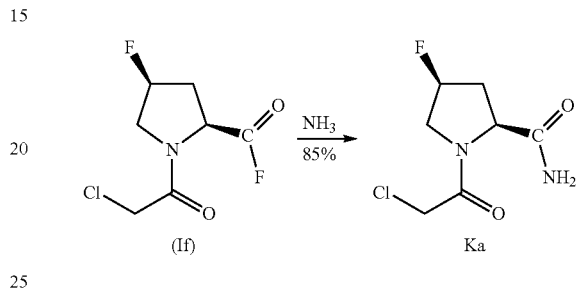

An aqueous 28-30% ammonia solution (NH$_3$, 10 mmol) was added, with vigorous stirring, to a solution of (2S,4S)—N-chloroacetyl-4-fluoropyrrolidine-2-carbonyl fluoride (If) (1.06 g, 5.0 mmol) in 10 mL of dichloromethane cooled on an ice water bath. After 10 minutes, the ice water bath was removed and stirring was continued for another 20 minutes at room temperature. Water (10 mL) was added to the reaction mixture. The reaction mixture was shaken well and then the dichloromethane layer removed. The aqueous layer was mixed with saturated brine solution and extracted with ethyl acetate (25 ml×3). Ethyl acetate layers were combined and dried over anhydrous magnesium sulfate and filtered. Removal of ethyl acetate at reduced pressure gave 886 mg (85% yield) of (2S,4S)—N-chloroacetyl-4-fluoropyrrolidine-2-carboxamide (Ka) as a white solid: $^{19}$F-NMR (CD$_3$CN) (a 1:3 mixture of two rotamers) δ −173.20 (m, ¼F), −173.85 (m, ¾F): $^1$H-NMR (CD$_3$CN) δ 2.1-3.0 (m, 2H), 3.6-4.2 (m, 4H), 4.55-4.8 (m, 2H), 5.2-5.8 (m, 1H), 6.1-6.8 (m, 2H): $^{13}$C-NMR (CD$_3$CN); a major rotamer: δ 35.56 (d, J=21.0 Hz), 42.92, 53.52 (d, J=23.8 Hz), 59.68, 93.24 (d, J=175.6 Hz), 166.08, 173.10.

Example 20

Reaction of (2S,4S)—N-Fmoc-4-fluoropyrrolidine-2-carboxamide (Fa) with trifluoroacetic anhydride; Preparation of (2S,4S)—N-Fmoc-4-fluoropyrrolidine-2-carbonitrile (Ia)

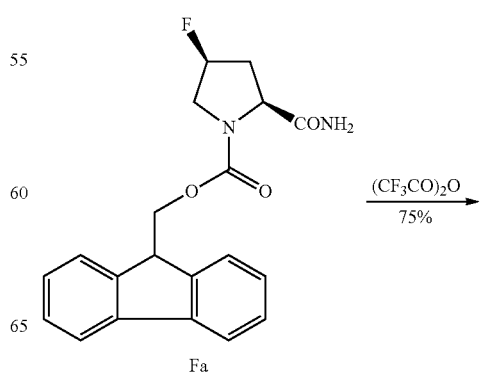

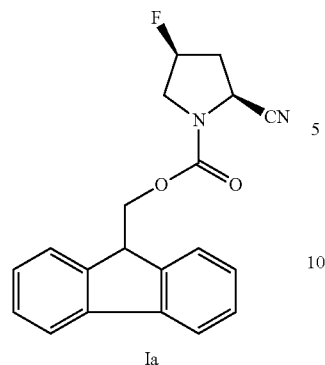

Ia (2S,4S)—N-Fmoc-4-fluoropyrrolidine-2-carboxamide (Fa) (1 mmol) was dissolved in 3 ml of dry THF and cooled on ice-water. Into the solution, trifluoroacetic anhydride (1.5 mmol) was added slowly. The reaction mixture was stirred at around 0° C. for 2 h. After reaction, all the volatiles were removed on vacuum to give a solid, which was crystallized from an ether/pentane mixture to give 250 mg (yield 75%) of (2S,4S)—N-Fmoc-4-fluoropyrrolidine-2-carbonitrile (Ia): $^{19}$F-NMR (CDCl$_3$) δ −174.63 (m): $^1$H-NMR (CDCl$_3$) δ 2.15-2.85 (m, 2H), 3.4-4.0 (m, 2H), 4.15-4.85 (m, 4H), 5.30 (d, 1H, J=51.2 Hz, 4-H), 7.27-7.85 (m, 8H): $^{13}$C-NMR (CDCl$_3$) (as a mixture of two rotamers) δ 90.90 (d, J=179.9 Hz, CF), 91.95 (d, J=179.9 Hz, CF), 117.92 (s, CN), 118.11 (s, CN), 153.54 (s, CON), 153.97 (s, CON).

Example 21

Reaction of (2S,4S)—N-(chloroacetyl)-4-fluoropyrrolidine-2-carboxamide (Ka) with trifluoroacetic anhydride; Preparation of (2S,4S)—N-chloroacetyl-4-fluoropyrrolidine-2-carbonitrile (La)

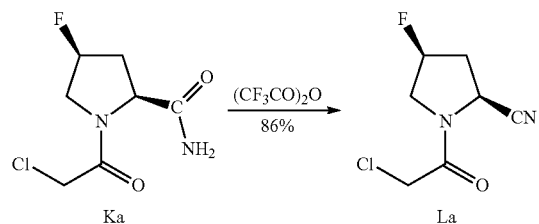

Into a solution of (2S,4S)—N-chloroacetyl-4-fluoropyrrolidine-2-carboxamide (Ka) (200 mg, 1.0 mmol) in 40 ml of anhydrous tetrahydronfuran was slowly added trifluoroacetic anhydride (315 mg, 1.5 mmol) at room temperature. The reaction mixture was stirred for 0.5 h at room temperature, and evaporated to dryness under vacuum. The resulting solid was crystallized from dichloromethane/pentane, giving 164 mg (86% yield) of (2S,4S)—N-chloroacetyl-4-fluoropyrrolidine-2-carbonitrile (La) as a white solid; mp 139-140° C. (recrystallized from dichloromethane/pentane): $^{19}$F-NMR (CDCl$_3$) δ −174.65 (m): $^1$H-NMR (CDCl$_3$) (a mixture of rotamers): δ 2.2-2.9 (m, 2H), 3.6-4.4 (m, 4H), 4.85-5.15 (m, 1H), 5.25-5.6 (m, 1H): $^{13}$C-NMR (CDCl$_3$); a major rotamer: δ 36.20 (d, J=21.7 Hz), 41.43, 45.47, 53.24 (d, J=24.6 Hz), 92.0 (d, J=182.0 Hz), 116.96, 165.28; a minor rotamer: 38.5 (d, J=21.5 Hz), 41.31, 45.19, 53.80 (d, J=24.5 Hz), 117.12, 165.00.

Example 22

Preparation of (2S,4S)-4-fluoropyrrolidine-2-carboxamide hydrochloride (Ga) from (2S,4S)—N-Fmoc-4-fluoropyrrolidine-2-carboxamide (Fa)

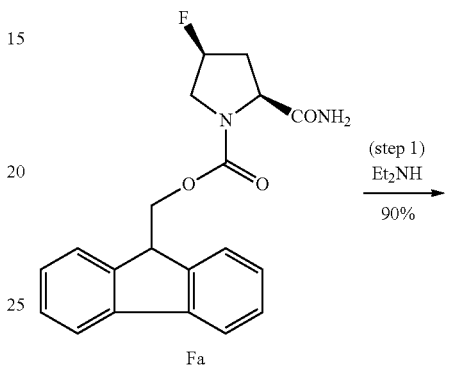

Fa

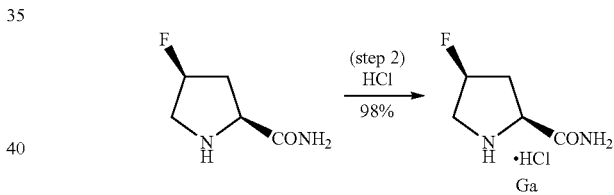

Ga

Step 1: (2S,4S)—N-Fmoc-4-fluoropyrrolidine-2-carboxamide (Fa) (354 mg, 1 mmol) was dissolved in 12 ml of a 1:1 mixture of diethylamine and dichloromethane at room temperature. After the mixture was stirred for 1.5 h, all the volatiles are removed. To the obtained residue was added ethyl acetate (10 ml) and water (5 mL), and the mixture was stirred and left. The aqueous layer was separated, washed with 10 ml of ethyl acetate, and evaporated to dryness by a vacuum pump. The residue was dissolved in 2 ml of isopropanol and mixed with ether. The precipitated solid was washed with ethyl acetate and dried in vacuo, giving 118 mg (yield 90%) of (2S,4S)-4-fluoropyrrolidine-2-carboxamide as crystals: $^{19}$F-NMR (D$_2$O) δ −172.40 (m, 1 F): $^1$H-NMR (D$_2$O) δ 2.0-2.5 (m, 2H), 2.95 (dd, 1H, J=38.8, 3.42 Hz), 3.20 (dd, 1H, J=21.6, 1.7 Hz), 3.0 (dd, 1H, J=10.3, 4.1 Hz), 5.16 (dt, 1H, J=53.2, 4.1 Hz): $^{13}$C-NMR (D$_2$O) δ 37.52 (d, J=21.7 Hz), 52.68 (d, J=23.1 Hz), 58.49, 94.63 (d, J=171.2 Hz, 4-C), 177.71 (CO).

Step 2: (2S,4S)-4-Fluoropyrrolidine-2-carboxamide (119 mg, 0.9 mmol) obtained in step 1 was dissolved in 5 ml of isopropanol. Into the solution, 1.5 mL (HCl 1.5 mmol) of 1.0 M HCl in ether was added, and after the mixture was stirred for 10 minutes, all the volatiles were removed. The resulting solid was dried in vacuum at 50° C. for 2 h, giving 148 mg (yield 98%) of (2S,4S)-4-fluoropyrrolidine-2-carboxamide hydrochloride (Ga). The product was identified by comparison with an authentic sample.

Example 23

Preparation of (2S,4S)-4-fluoropyrrolidine-2-carbonitrile hydrochloride (Ia) from (2S,4S)—N-Fmoc-4-fluoropyrrolidine-2-carbonitrile (Ja)

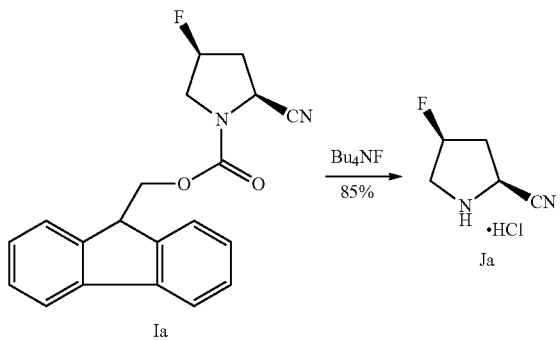

(2S,4S)—N-Fmoc-4-fluoropyrrolidine-2-carbonitrile (Ia) (336 mg, 1.0 mmol) was dissolved in 1 ml of DMF, and a solution of 4 mmol of tetrabutylammonium fluoride in 3 ml of THF was added at room temperature. After stirring for 10 min at room temperature, methanol (8 ml) was added and stirring was continued for 3 h. 48% aqueous HF (10 ml) was added followed by addition of 10 ml of water. The aqueous layer was washed with 25 ml of ethyl acetate twice. The aqueous layer was neutralized with 1 N NaOH solution (to pH-8) and extracted with ethyl acetate. The ethyl acetate solution was dried over anhydrous $MgSO_4$ and filtered, and the filtrate was mixed with 10 ml of 1M HCl aqueous solution. The aqueous layer was separated out and concentrated in vacuum to give the desired product as hydrochloride salt (Ja), which was then washed with ethyl acetate to remove traces of DMF and tetrabutylammonium chloride. Yield 85%. $^{19}$F-NMR ($D_2O$) δ −175.35 (m, 1 F): $^1$H-NMR ($D_2O$) δ 2.42-2.75 (m, 2H), 3.40 (dd, 1H, J=34.0, 3.0 Hz), 3.71 (dd, 1H, J=17.5, 2.0 Hz), 3.0 (dd, 1H, J=10.3, 4.1 Hz), 4.8-4.95 (m, 1H), 5.45 (dt, 1H, J=50.8, 3.5 Hz): $^{13}$C-NMR ($D_2O$) δ 37.52 (d, J=21.7 Hz), 52.68 (d, J=23.1 Hz), 58.49, 94.63 (d, J=171.2 Hz), 177.71.

Example 24

Preparation of trimethylsilyl (2S,4R)—N-chloroacetyl-4-(trimethylsilyloxy)-pyrrolidine-2-carboxylate

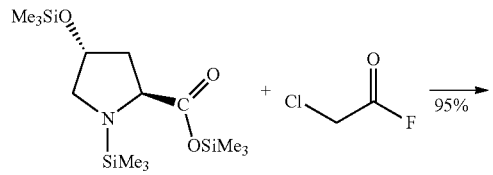

-continued

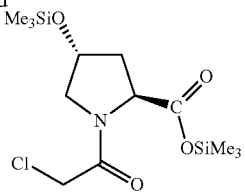

Into a solution of trimethylsilyl (2S,4R)—N-trimethylsilyl-4-(trimethylsilyloxy)-pyrrolidine-2-carboxylate (5.22 g, 15.0 mmol) in 15 ml of anhydrous dichloromethane was drop wise added a solution of chloroacetyl fluoride in 5 ml of dichloromethane with vigorous stirring at room temperature. Exothermic reaction occurred with liberation of $Me_3SiF$. The reaction mixture was stirred at room temperature for 2 h and then the reaction mixture was evaporated to dryness at reduced pressure, which gave 5.02 g (yield 95%) of trimethylsilyl (2S,4R)—N-chloroacetyl-4-(trimethylsilyloxy)pyrrolidine-2-carboxylate as off-white solid: $^1$H-NMR ($CDCl_3$) δ 0.02 (m, 9H), 0.19 (m, 9H), 1.80-2.4 (m, 2H), 3.3-3.8 (m, 2H), 3.8-4.0 (m, 2H), 4.2-4.6 (m, 2H): $^{13}$C-NMR ($CDCl_3$) δ −0.32 (CSi), −0.05 (CSi), 37.91, 41.81, 55.30, 59.21, 70.31, 165.13, 171.78.

Example 25

Preparation of (2S,4R)—N-(chloroacetyl)-4-hydroxypyrrolidine-2-carboxylic acid

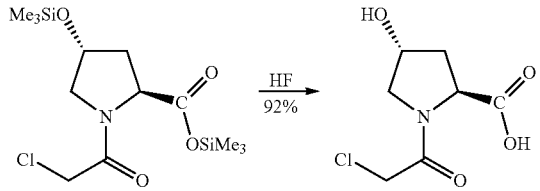

Anhydrous HF with nitrogen gas was bubbled into a solution of trimethylsilyl (2S,4R)—N-(chloroacetyl)-4-(trimethylsilyloxy)pyrrolidine-2-carboxylate (4.70 g, 15.0 mmol) in 20 ml of acetonitrile in a Teflon container [HF was generated by heating 10 g (100 mmol) of NaF.HF at 215° C. in a Teflon® vessel and carried with nitrogen flow into the solution]. The reaction mixture was then stirred at room temperature for 15 h. The reaction mixture was evaporated to dryness in vacuo. The resulting solid was washed with 100 ml of anhydrous ether and dried in vacuo to yield 2.67 g (yield 92%) of (2S, 4R)—N-(chloroacetyl)-4-hydroxypyrrolidine-2-carboxylic acid as a off-white solid: mp 123-124° C. (dec): $^1$H-NMR ($D_2O$) δ 1.9-2.4 (m, 2H), 3.4-3.7 (m, 2H), 3.9-4.2 (m, 2H), 4.25-4.5 (m, 2H): $^{13}$C-NMR ($CDCl_3$) δ 36.65, 41.84, 54.87, 58.36, 69.79, 168.22, 175.30: High Resolution Mass/ESI- APCI method; (M+H)+ 208.0369 (calcd 208.0371 for C7H11ClNO4); (M+Na)+ 230.0189 [calcd 230.0191 for (C7H10ClNO4+Na)].

Example 26

Preparation of (2S,4R)—N-(chloroacetyl)-4-pyrrolidine-2-carboxylic acid

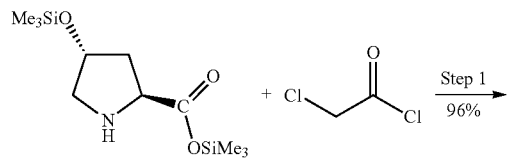

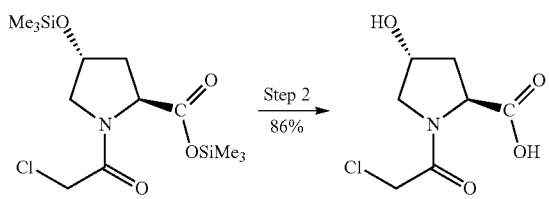

Step 1: A solution of chloroacetyl chloride (1.0 mL, 12.6 mmol) in 1 mL of dichloromethane was added slowly into a stirred solution of trimethylsilyl (2S,4R)-4-(trimethylsilyloxy)pyrrolidine-2-carboxylate (3.62 g, 13.1 mmol) [which was contaminated with trimethylsilyl (2R,4R)-4-(trimethylsilyloxy)pyrrolidine-2-carboxylate in about 20% content] and di(isopropyl)ethylamine (3 ml, 17.2 mmol) in 100 mL of dry dichloromethane cooled on an ice bath. An additional 1.0 ml of di(isopropyl)ethylamine was added and the mixture was stirred an additional 30 minutes on the ice bath. The reaction solution was then evaporated to dryness by a vacuum pump. The residue was slurried in pentane and filtered. The filtrate was then evaporated by a vacuum pump to yield 4.26 g (96% crude yield) of crude trimethylsilyl (2S,4R)—N-chloroacetyl-4-(trimethylsilyloxy)pyrrolidine-2-carboxylate as an oil, which solidified upon cooling.

Step 2: Approximately 20 ml of anhydrous 1N HCl/Et2O solution was then added to the crude product, resulting in an immediate precipitate, and the reaction mixture was stirred overnight. The ether was decanted off, and the solid was washed once with fresh ether, which was again decanted off. Upon drying with vacuum, 2.25 g (86% yield) of (2S,4R)—N-chloroacetyl-4-hydroxypyrrolidine-2-carboxylic acid as yellow powder was obtained. The product was further purified by washing with a small amount of dry acetonitrile. Spectral data of the product were in agreement with those of the product obtained in Example 25.

Example 27

Preparation of trimethylsilyl (2S,4R)—N-(bromoacetyl)-4-(trimethylsilyloxy)pyrrolidine-2-carboxylate

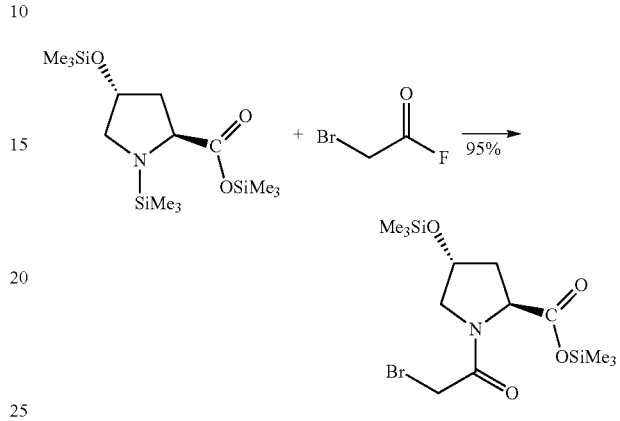

Into a solution of trimethylsilyl (2S,4R)—N-(trimethylsilyl)-4-(trimethylsilyloxy)-pyrrolidine-2-carboxylate (6.95 g, 20.0 mmol) in 15 ml of anhydrous dichloromethane was drop wise added a solution of bromoacetyl fluoride (2.82 g, 20.0 mmol) in 5 ml of dichloromethane with vigorous stirring at room temperature. Exothermic reaction occurred with liberation of Me3SiF. The reaction mixture was stirred at room temperature for 2 h and then the reaction mixture was evaporated to dryness at reduced pressure, which gave 7.53 g (yield 95%) of trimethylsilyl (2S,4R)—N-(bromoacetyl)-4-(trimethylsilyloxy)pyrrolidine-2-carboxylate as off-white solid: $^1$H-NMR (CDCl3) δ 0.04 (m, 9H), 0.21 (m, 9H), 1.80-2.4 (m, 2H), 3.3-3.6 (m, 1H), 3.61-3.80 (m, 2H), 4.3-4.6 (m, 2H); $^{13}$C-NMR (CDCl3) δ −0.27 (CSi), −0.01 (CSi), 26.94, 38.04, 55.71, 59.26, 70.33, 165.28, 171.82.

All references including publications and patents are incorporated by reference herein for all purposes.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:
1. A 4-fluoropyrrolidine-2-carbonyl fluoride compound having a formula (I) as follows:

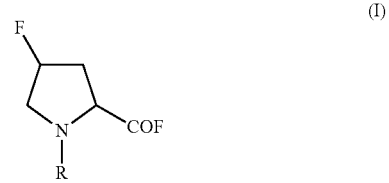

(I)

in which R is a substituted or unsubstituted alkoxycarbonyl group having 2 to 35 carbon atoms, a substituted or unsubstituted aryloxycarbonyl group having 7 to 35 carbon atoms, a substituted or unsubstituted acyl group having 1 to 35 carbon atoms, a substituted or unsubstituted alkanesulfonyl group having 1 to 35 carbon atoms, a substituted or unsubstituted arenesulfonyl group having 6 to 35 carbon atoms, a substituted or unsubstituted alkyl group having 1 to 35 carbon atoms, or a substituted or unsubstituted aryl group having 6 to 35 carbon atoms.

2. The 4-fluoropyrrolidine-2-carbonyl fluoride compound of claim 1 wherein R is a substituted or unsubstituted alkoxycarbonyl group having 2 to 15 carbon atoms, a substituted or unsubstituted aryloxycarbonyl group having 7 to 15 carbon atoms, a substituted or unsubstituted acyl group having 1 to 15 carbon atoms, a substituted or unsubstituted alkanesulfonyl group having 1 to 15 carbon atoms, a substituted or unsubstituted arenesulfonyl group having 6 to 15 carbon atoms, a substituted or unsubstituted alkyl group having 1 to 15 carbon atoms, or a substituted or unsubstituted aryl group having 6 to 15 carbon atoms.

3. The 4-fluoropyrrolidine-2-carbonyl fluoride compound of claim 1 wherein R is a substituted or unsubstituted alkoxycarbonyl group having 2 to 15 carbon atoms or a substituted or unsubstituted acyl group having 1 to 15 carbon atoms.

4. The 4-fluoropyrrolidine-2-carbonyl fluoride compound of claim 1 selected from a group consisting of: (2S,4S)—N-(9-fluorenylmethoxycarbonyl)-4-fluoropyrrolidine-2-carbonyl fluoride, (2R,4R)—N-(9-fluorenylmethoxycarbonyl)-4-fluoropyrrolidine-2-carbonyl fluoride, (2S,4R)—N-(9-fluorenylmethoxycarbonyl)-4-fluoropyrrolidine-2-carbonyl fluoride, (2R,4S)—N-(9-fluorenylmethoxycarbonyl)-4-fluoropyrrolidine-2-carbonyl fluoride, racemic N-(9-fluorenylmethoxycarbonyl)-cis-4-fluoropyrrolidine-2-carbonyl fluoride, racemic N-(9-fluorenylmethoxycarbonyl)-trans-4-fluoropyrrolidine-2-carbonyl fluoride, (2S,4S)—N-(benzyloxycarbonyl)-4-fluoropyrrolidine-2-carbonyl fluoride, (2R,4R)—N-(benzyloxycarbonyl)-4-fluoropyrrolidine-2-carbonyl fluoride, (2S,4R)—N-(benzyloxycarbonyl)-4-fluoropyrrolidine-2-carbonyl fluoride, (2R,4S)—N-(benzyloxycarbonyl)-4-fluoropyrrolidine-2-carbonyl fluoride, racemic N-(benzyloxycarbonyl)-cis-4-fluoropyrrolidine-2-carbonyl fluoride, racemic N-(benzyloxycarbonyl)-trans-4-fluoropyrrolidine-2-carbonyl fluoride, (2S,4S)—N-(tert-butoxycarbonyl)-4-fluoropyrrolidine-2-carbonyl fluoride, (2R,4R)—N-(tert-butoxycarbonyl)-4-fluoropyrrolidine-2-carbonyl fluoride, (2S,4R)—N-(tert-butoxycarbonyl)-4-fluoropyrrolidine-2-carbonyl fluoride, (2R,4S)—N-(tert-butoxycarbonyl)-4-fluoropyrrolidine-2-carbonyl fluoride, racemic N-(tert-butoxycarbonyl)-cis-4-fluoropyrrolidine-2-carbonyl fluoride, racemic N-(tert-butoxycarbonyl)-trans-4-fluoropyrrolidine-2-carbonyl fluoride, (2S,4S)—N-chloroacetyl-4-fluoropyrrolidine-2-carbonyl fluoride, (2R,4R)—N-chloroacetyl-4-fluoropyrrolidine-2-carbonyl fluoride, (2S,4R)—N-chloroacetyl-4-fluoropyrrolidine-2-carbonyl fluoride, (2R,4S)—N-chloroacetyl-4-fluoropyrrolidine-2-carbonyl fluoride, racemic N-chloroacetyl-cis-4-fluoropyrrolidine-2-carbonyl fluoride, racemic N-chloroacetyl-trans-4-fluoropyrrolidine-2-carbonyl fluoride, (2S,4S)—N-bromoacetyl-4-fluoropyrrolidine-2-carbonyl fluoride, (2R,4R)—N-bromoacetyl-4-fluoropyrrolidine-2-carbonyl fluoride, (2S,4R)—N-bromoacetyl-4-fluoropyrrolidine-2-carbonyl fluoride, (2R,4S)—N-bromoacetyl-4-fluoropyrrolidine-2-carbonyl fluoride, racemic N-bromoacetyl-cis-4-fluoropyrrolidine-2-carbonyl fluoride, racemic N-bromoacetyl-trans-4-fluoropyrrolidine-2-carbonyl fluoride, (2S,4S)—N-iodoacetyl-4-fluoropyrrolidine-2-carbonyl fluoride, (2R,4R)—N-iodoacetyl-4-fluoropyrrolidine-2-carbonyl fluoride, (2S,4R)—N-iodoacetyl-4-fluoropyrrolidine-2-carbonyl fluoride, (2R,4S)—N-iodoacetyl-4-fluoropyrrolidine-2-carbonyl fluoride, racemic N-iodoacetyl-cis-4-fluoropyrrolidine-2-carbonyl fluoride, and racemic N-iodoacetyl-trans-4-fluoropyrrolidine-2-carbonyl fluoride.

5. The 4-fluoropyrrolidine-2-carbonyl fluoride compound of claim 1 selected from a group consisting of: (2S,4S)—N-(9-fluorenylmethoxycarbonyl)-4-fluoropyrrolidine-2-carbonyl fluoride, (2S,4R)—N-(9-fluorenylmethoxycarbonyl)-4-fluoropyrrolidine-2-carbonyl fluoride, (2S,4S)—N-(benzyloxycarbonyl)-4-fluoropyrrolidine-2-carbonyl fluoride, (2S,4R)—N-(benzyloxycarbonyl)-4-fluoropyrrolidine-2-carbonyl fluoride, (2S,4S)—N-(tert-butoxycarbonyl)-4-fluoropyrrolidine-2-carbonyl fluoride, (2S,4R)—N-(tert-butoxycarbonyl)-4-fluoropyrrolidine-2-carbonyl fluoride, (2S,4S)—N-chloroacetyl-4-fluoropyrrolidine-2-carbonyl fluoride, (2S,4R)—N-chloroacetyl-4-fluoropyrrolidine-2-carbonyl fluoride, (2S,4S)—N-bromoacetyl-4-fluoropyrrolidine-2-carbonyl fluoride, (2S,4R)—N-bromoacetyl-4-fluoropyrrolidine-2-carbonyl fluoride.

6. The 4-fluoropyrrolidine-2-carbonyl fluoride compound of claim 1 selected from a group consisting of: (2S,4S)—N-(9-fluorenylmethoxycarbonyl)-4-fluoropyrrolidine-2-carbonyl fluoride, (2S,4S)—N-(benzyloxycarbonyl)-4-fluoropyrrolidine-2-carbonyl fluoride, (2S,4S)—N-(tert-butoxycarbonyl)-4-fluoropyrrolidine-2-carbonyl fluoride, and (2S,4S)—N-(chloroacetyl)-4-fluoropyrrolidine-2-carbonyl fluoride.

7. A method for preparing a 4-fluoropyrrolidine-2-carbonyl fluoride compound having a formula (I) as follows:

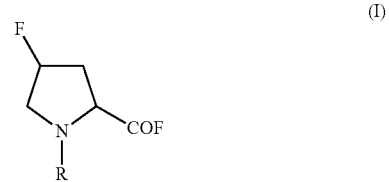

the method comprising reacting a 4-hydroxypyrrolidine-2-carboxylic acid compound having a formula (II) with a fluorinating agent:

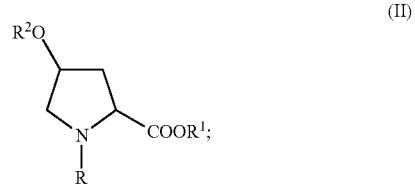

in which R is a substituted or unsubstituted alkoxycarbonyl group having 2 to 35 carbon atoms, a substituted or unsubstituted aryloxycarbonyl group having 7 to 35 carbon atoms, a substituted or unsubstituted acyl group having 1 to 35 carbon atoms, a substituted or unsubstituted alkanesulfonyl group having 1 to 35 carbon atoms, a substituted or unsubstituted arenesulfonyl group having 6 to 35 carbon atoms, a substituted or unsubstituted alkyl group having 1 to 35 carbon atoms, or a substituted or unsubstituted aryl group having 6 to 35; and $R^1$ and $R^2$ each is independently a hydrogen atom or a $SiR^3R^4R^5$ group, in which $R^3$, $R^4$, and $R^5$ each is independently an alkyl group having 1 to 4 carbon atoms, an aralkyl group having 6 to 10 carbon atoms, or an aryl group having 6 to 10 carbon atoms.

8. The method of claim 7 wherein the fluorinating agent is a compound that undertakes a deoxo-fluorination reaction.

9. The method of claim 7 wherein the fluorinating agent is selected from a group consisting of: substituted or unsubstituted phenylsulfur trifluorides, substituted (diamino)difluoromethanes, substituted α,α-difluoroalkylamines, substituted aminosulfur trifluorides, and sulfur tetrafluoride.

10. The method of claim 7 wherein the fluorinating agent is a substituted or unsubstituted phenylsulfur trifluoride having a formula (III):

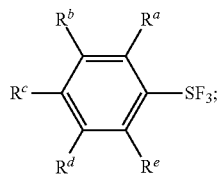

(III)

in which $R^a$, $R^b$, $R^c$, $R^d$, and $R^e$ each is independently a hydrogen atom, a halogen atom, a substituted or unsubstituted alkyl group having 1 to 10 carbon atoms, a nitro group, or a cyano group.

11. The method of claim 7 wherein the fluorinating agent is selected from a group consisting of phenylsulfur trifluoride, 4-methylphenylsulfur trifluoride, 4-(tert-butyl)phenylsulfur trifluoride, 4-(tert-butyl)-2,6-dimethylphenylsulfur trifluoride, 4-fluorophenylsulfur trifluoride, 4-chlorophenylsulfur trifluoride, 2,2-difluoro-1,3-dimethylimizadolidine, $ClCHFCF_2N(CH_2CH_3)_2$ (Yarovenko reagent), $CF_3CHFCF_2N(CH_2CH_3)_2$ (Ishikawa reagent), $CHF_2CF_2N(CH_3)_2$, dimethylaminosulfur trifluoride, diethylaminosulfur trifluoride, and bis(methoxyethyl)aminosulfur trifluoride.

12. The method of claim 7 wherein the fluorinating agent is 4-(tert-butyl)-2,6-dimethylphenylsulfur trifluoride.

13. A N-haloacetyl-4-hydroxypyrrolidine-2-carboxylic acid compound having a formula (II') as follows:

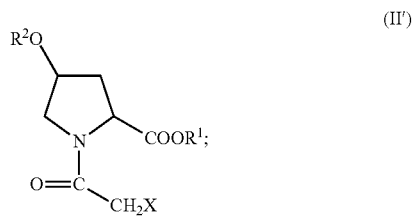

(II')

in which X is a halogen atom; and $R^1$ and $R^2$ each is independently a hydrogen atom or a $SiR^3R^4R^5$ group wherein $R^3$, $R^4$, and $R^5$ each is independently an alkyl group having 1 to 4 carbon atoms, an aralkyl group having 6 to 10 carbon atoms, or an aryl group having 6 to 10 carbon atoms.

14. The N-haloacetyl-4-hydroxypyrrolidine-2-carboxylic acid compound of claim 13 selected from a group consisting of: (2S,4S)—N-(chloroacetyl)-4-hydroxypyrrolidine-2-carboxylic acid, (2S,4R)—N-(chloroacetyl)-4-hydroxypyrrolidine-2-carboxylic acid, trimethylsilyl (2S,4S)—N-(chloroacetyl)-4-(trimethylsilyloxy)pyrrolidine-2-carboxylate, trimethylsilyl (2S,4R)—N-(chloroacetyl)-4-(trimethylsilyloxy)pyrrolidine-2-carboxylate, (2S,4S)—N-(bromoacetyl)-4-hydroxypyrrolidine-2-carboxylic acid, (2S,4R)—N-(bromoacetyl)-4-hydroxypyrrolidine-2-carboxylic acid, trimethylsilyl (2S,4S)—N-(bromoacetyl)-4-(trimethylsilyloxy)pyrrolidine-2-carboxylate, trimethylsilyl (2S,4R)—N-(bromoacetyl)-4-(trimethylsilyloxy)pyrrolidine-2-carboxylate, (2S,4S)—N-(iodoacetyl)-4-hydroxypyrrolidine-2-carboxylic acid, (2S,4R)—N-(iodoacetyl)-4-hydroxypyrrolidine-2-carboxylic acid, trimethylsilyl (2S,4S)—N-(iodoacetyl)-4-(trimethylsilyloxy)pyrrolidine-2-carboxylate, and trimethylsilyl (2S,4R)—N-(iodoacetyl)-4-(trimethylsilyloxy)pyrrolidine-2-carboxylate.

15. The N-haloacetyl-4-hydroxypyrrolidine-2-carboxylic acid compound of claim 13 selected from a group consisting of: (2S,4R)—N-(chloroacetyl)-4-hydroxypyrrolidine-2-carboxylic acid, trimethylsilyl (2S,4R)—N-(chloroacetyl)-4-(trimethylsilyloxy)pyrrolidine-2-carboxylate, (2S,4R)—N-(bromoacetyl)-4-hydroxypyrrolidine-2-carboxylic acid, and trimethylsilyl (2S,4R)—N-(bromoacetyl)-4-(trimethylsilyloxy)pyrrolidine-2-carboxylate.

* * * * *